US011650197B2

(12) United States Patent
Kluckner et al.

(10) Patent No.: US 11,650,197 B2
(45) Date of Patent: May 16, 2023

(54) METHODS AND APPARATUS ADAPTED TO QUANTIFY A SPECIMEN FROM MULTIPLE LATERAL VIEWS

(71) Applicant: Siemens Healthcare Diagnostics Inc., Tarrytown, NY (US)

(72) Inventors: Stefan Kluckner, Berlin (DE); Yao-Jen Chang, Princeton, NJ (US); Terrence Chen, Princeton, NJ (US); Benjamin S. Pollack, Jersey City, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1210 days.

(21) Appl. No.: 16/072,394

(22) PCT Filed: Jan. 24, 2017

(86) PCT No.: PCT/US2017/014772
§ 371 (c)(1),
(2) Date: Jul. 24, 2018

(87) PCT Pub. No.: WO2017/132166
PCT Pub. Date: Aug. 3, 2017

(65) Prior Publication Data
US 2019/0033209 A1 Jan. 31, 2019

Related U.S. Application Data

(60) Provisional application No. 62/288,362, filed on Jan. 28, 2016.

(51) Int. Cl.
*G01N 21/31* (2006.01)
*G06T 7/00* (2017.01)
(Continued)

(52) U.S. Cl.
CPC ............. *G01N 21/31* (2013.01); *G01F 23/00* (2013.01); *G01N 21/90* (2013.01); *G01N 33/49* (2013.01);
(Continued)

(58) Field of Classification Search
USPC ......................................................... 702/21
See application file for complete search history.

(56) References Cited

U.S. PATENT DOCUMENTS 3,905,045 A * 9/1975 Nickel ..................... A61B 6/02
382/294
4,100,416 A * 7/1978 Hirschfeld ......... G01N 33/5302
436/805
(Continued)

FOREIGN PATENT DOCUMENTS

| CN | 101526465 A | 9/2009 |
|----|-------------|--------|
| CN | 102027350 A | 4/2011 |

(Continued)

OTHER PUBLICATIONS

PCT International Search Report and Written Opinion dated Apr. 10, 2017 (10 Pages).

(Continued)

Primary Examiner — Kathleen Y Dulaney

(57) ABSTRACT

A model-based method for quantifying a specimen. The method includes providing a specimen, capturing images of the specimen while illuminated by multiple spectra at different nominal wavelengths, and exposures, and classifying the specimen into various class types comprising one or more of serum or plasma portion, settled blood portion, gel separator (if used), air, tube, label, or cap; and quantifying of the specimen. Quantifying includes determining one or more of: a location of a liquid-air interface, a location of a serum-blood interface, a location of a serum-gel interface, a location of a blood-gel interface, a volume and/or a depth of (Continued)

the serum or plasma portion, or a volume and/or a depth of the settled blood portion. Quality check modules and specimen testing apparatus adapted to carry out the method are described, as are other aspects.

17 Claims, 8 Drawing Sheets

(51) Int. Cl.
- *G06T 7/62* (2017.01)
- *G01F 23/00* (2022.01)
- *G01N 33/49* (2006.01)
- *G01N 21/90* (2006.01)
- *G01N 35/00* (2006.01)
- *G01N 35/04* (2006.01)
- *G06K 9/62* (2022.01)
- *G06N 7/08* (2006.01)
- *G01N 35/02* (2006.01)
- *G01N 21/17* (2006.01)

(52) U.S. Cl.
CPC ..... *G01N 33/491* (2013.01); *G01N 35/00732* (2013.01); *G01N 35/04* (2013.01); *G06K 9/628* (2013.01); *G06K 9/6269* (2013.01); *G06N 7/08* (2013.01); *G06T 7/0012* (2013.01); *G06T 7/62* (2017.01); *G01N 35/0099* (2013.01); *G01N 35/02* (2013.01); *G01N 2021/1772* (2013.01); *G01N 2021/1776* (2013.01); *G01N 2035/00495* (2013.01); *G01N 2035/00752* (2013.01); *G01N 2035/0406* (2013.01); *G01N 2035/0439* (2013.01); *G06T 2207/10016* (2013.01); *G06T 2207/10024* (2013.01); *G06T 2207/10144* (2013.01); *G06T 2207/10152* (2013.01); *G06T 2207/20081* (2013.01); *G06T 2207/20084* (2013.01); *G06T 2207/30024* (2013.01)

(56) References Cited

U.S. PATENT DOCUMENTS

| | | | |
|---|---|---|---|
| 5,764,792 A | 6/1998 | Kennealy | |
| 6,587,575 B1* | 7/2003 | Windham | A22B 5/007 382/110 |
| 7,952,693 B2* | 5/2011 | Serebrennikova | G01N 21/474 356/39 |
| 8,280,140 B2* | 10/2012 | Levenson | G06K 9/628 600/407 |
| 9,880,082 B2* | 1/2018 | Esaki | G01N 15/042 |
| 10,311,569 B1* | 6/2019 | Bhatia | G06T 7/0014 |
| 10,527,635 B1* | 1/2020 | Bhatia | G01N 35/04 |
| 10,746,665 B2 | 8/2020 | Kluckner et al. | |
| 10,816,538 B2 | 10/2020 | Kluckner et al. | |
| 10,928,310 B2 | 2/2021 | Wissmann et al. | |
| 11,042,788 B2 | 6/2021 | Kluckner et al. | |
| 2005/0163354 A1 | 7/2005 | Ziegler | |
| 2006/0001870 A1* | 1/2006 | Voigt | G01N 21/65 356/301 |
| 2006/0148096 A1* | 7/2006 | Jina | G01N 33/723 436/514 |
| 2006/0155193 A1* | 7/2006 | Leonardi | A61B 5/0075 600/473 |
| 2008/0082468 A1 | 4/2008 | Long et al. | |
| 2008/0144898 A1* | 6/2008 | Hunt | G06V 20/69 382/128 |
| 2010/0027868 A1* | 2/2010 | Kosaka | G01N 35/1016 382/134 |
| 2011/0234757 A1* | 9/2011 | Zheng | G02B 21/0008 348/46 |
| 2011/0304820 A1* | 12/2011 | Falt | G06T 5/50 351/246 |
| 2012/0067960 A1* | 3/2012 | Rowe | G06K 19/06159 235/494 |
| 2012/0138674 A1 | 6/2012 | Chen | |
| 2012/0140230 A1* | 6/2012 | Miller | G06T 7/0012 356/432 |
| 2012/0169863 A1 | 7/2012 | Bachelet et al. | |
| 2012/0263369 A1 | 10/2012 | Xie et al. | |
| 2012/0302892 A1* | 11/2012 | Lue | A61B 5/0071 600/476 |
| 2012/0309636 A1* | 12/2012 | Gibbons | C12Q 1/6809 435/6.12 |
| 2014/0193050 A1* | 7/2014 | Miller | G06T 5/50 382/128 |
| 2014/0368631 A1* | 12/2014 | Wardlaw | G02B 21/365 348/79 |
| 2015/0018644 A1* | 1/2015 | Gulati | G01J 3/0218 600/316 |
| 2015/0092200 A1 | 4/2015 | Zahniser et al. | |
| 2015/0198591 A1* | 7/2015 | Patel | G01N 33/6854 435/7.25 |
| 2015/0221088 A1* | 8/2015 | Satish | G16Z 99/00 382/134 |
| 2015/0241457 A1* | 8/2015 | Miller | G01N 21/84 382/103 |
| 2016/0109350 A1* | 4/2016 | Esaki | G01N 15/042 356/39 |
| 2016/0249836 A1* | 9/2016 | Gulati | G01N 21/359 600/316 |
| 2017/0227493 A1* | 8/2017 | Tsai | G01N 27/44726 |
| 2017/0339363 A1* | 11/2017 | Hiasa | H04N 5/378 |
| 2018/0372648 A1 | 12/2018 | Wissmann et al. | |

FOREIGN PATENT DOCUMENTS

| | | |
|---|---|---|
| CN | 103477197 A | 12/2013 |
| CN | 104459098 A | 3/2015 |
| JP | H09-133687 A | 5/1997 |
| JP | 2001-153625 A | 6/2001 |
| JP | 2004-037322 A | 2/2004 |
| JP | 2005 345370 A | 12/2005 |
| JP | 2012-159318 A | 8/2012 |
| JP | 2013-501937 A | 1/2013 |
| WO | 2008079590 A1 | 7/2008 |
| WO | 2012125291 A1 | 9/2012 |
| WO | 2015072358 A1 | 10/2014 |
| WO | 2015109263 A2 | 7/2015 |

OTHER PUBLICATIONS

Extended EP Search Report dated Nov. 14, 2018 of corresponding European Application No. 17744777.8, 5 Pages.
A. Laurentini "The visual hull concept for silhouette-based image understanding" IEEE Trans. Pattern Analysis and Machine Intelligence. pp. 150-162, 1994.

* cited by examiner

METHODS AND APPARATUS ADAPTED TO QUANTIFY A SPECIMEN FROM MULTIPLE LATERAL VIEWS

RELATED APPLICATION

This application claims priority to U.S. Provisional Patent Application Ser. No. 62/288,362 entitled "METHODS AND APPARATUS ADAPTED TO QUANTIFY A SPECIMEN FROM MULTIPLE LATERAL VIEWS" filed on Jan. 28, 2016, the disclosure of which is hereby incorporated by reference in its entirety herein.

FIELD

The present invention relates to methods and apparatus for testing of a specimen, and, more particularly, to methods and apparatus for determining amounts of various components contained in the specimen.

BACKGROUND

Automated testing systems may conduct assays or clinical analysis using one or more reagents to identify an analyte or other constituent in a specimen such as urine, blood serum, blood plasma, interstitial liquid, cerebrospinal liquids, and the like. For convenience and safety reasons, such specimens are usually contained within specimen containers (e.g., specimen collection tubes). The testing reactions generate various changes that may be read and/or manipulated to determine a concentration of analyte or other constituent contained in the specimen, that may in some embodiments be indicative of a patent's disease state.

Improvements in automated testing technology have been accompanied by corresponding advances in pre-analytical specimen preparation and handling operations such as sorting, batch preparation, centrifuging of specimen containers to separate specimen components, cap removal to facilitate fluid access, and the like by automated specimen preparation systems called Laboratory Automation Systems (LASs). LASs may also automatically transport a specimen in a specimen container to a number of specimen processing stations so that various operations (e.g., pre-analytical or analytical tests) can be performed thereon.

LASs may handle a number of different specimens contained in standard, barcode-labeled specimen containers, which may be of different sizes. The barcode label may contain an accession number that may contain or be correlated to patient information other information that may be entered into a hospital's Laboratory Information System (LIS) along with test orders and other desired information. An operator may place the labeled specimen containers onto the LAS system, which may automatically route the specimen containers for pre-analytical operations such as centrifugation, de-capping, and/or aliquot preparation, and all prior to the specimen actually being subjected to clinical analysis or assaying by one or more analyzers (clinical chemistry or assaying instruments) that may also be part of the LAS.

For certain tests, a serum or plasma portion (obtained from whole blood by centrifugation) may be used. A gel separator may be added to the specimen container to aid in the separation of a settled blood portion from the serum or plasma portion in some cases. After centrifuging and a subsequent de-capping process, the specimen container may be transported to an appropriate analyzer that may extract serum or plasma portion of the specimen from the specimen container and combine the serum or plasma portion with one or more reagents in a reaction vessel (e.g., cuvette). Analytical measurements may then be performed, often using a beam of interrogating radiation, for example, or by using photometric or fluorometric absorption readings, or the like. The measurements allow determination of end-point or rate or other values, from which an amount of analyte or other constituent is determined using well-known techniques.

Unfortunately, the determination of the demarcation between the various portions (e.g., settled portion, serum or plasma portion, and gel separator (if used)) in the specimen may be difficult to determine using existing methods. Thus, the volume of the resultant serum or plasma portion or the relative amounts of settled portion and serum or plasma portion may be difficult to determine, or simply not determined.

Previously, the location of the liquid-air interface of the serum or plasma portion of the specimen may be determined by a depth sensor (e.g., via a capacitive probe measurement or monitoring aspiration pressure as the probe descends). Based on this, the probe (otherwise referred to as a "pipette") may be lowered a predetermined amount below the surface of the serum or plasma portion and aspiration may commence. However, not knowing the amount of serum or plasma portion available, especially when multiple tests are ordered on the patient's specimen, may result in fouling of the probe. If the probe is lowered too much, the probe may be fouled with settled blood portion or gel separator, which may require tip replacement or stopping the analyzer to clean the probe.

Because the LA interface detection includes the problems listed above, it is desired to evaluate the sizes of the various portions of the specimen without the use of capacitive or pressure based methods, but via an automated optical inspection method. However, in some instances, barcode labels adhered directly to the specimen container may partially occlude the specimen, so that there may not be a clear opportunity to visually observe the serum or plasma portion. Furthermore, fairly large color deviations may be present between specimens including hemolysis, icterus, and lipemia further complicating the detection of the lines of demarcation.

Other systems, such as those described in US Pat. Pub. No. 2012/0140230 to Miller describe rotating the specimen container to find a view window that is unobstructed by the label and then measuring the relative amounts of the components using an optical imaging system. However, such systems may be less prone to ease of automation.

Because of the difficulties encountered in determining the amounts of the various components contained in the specimen, there is an unmet need for a method and apparatus adapted to readily determine a volume of each component and/or a precise location of the demarcation between the components. The method and apparatus should not appreciably adversely affect the speed of obtaining an analytical test result, i.e., slow appreciably the overall testing process taking place on the LAS. Furthermore, the method and apparatus should be able to be used even on labeled specimen containers, where one or more labels occlude some portion of the specimen.

SUMMARY

According to a first aspect, a method of quantifying a specimen contained within a specimen container is provided. The method includes providing a specimen, capturing images of the specimen at multiple spectra having different nominal wavelengths and at multiple different exposures, selection of optimally-exposed pixels from the images at the multiple different exposures at each of the multiple spectra to generate optimally-exposed image data for each of the multiple spectra, classifying the specimen into various class types comprising one or more of serum or plasma portion, settled blood portion, gel separator, if the gel separator is used, air, tube, label, or cap, and computing one or more of: a location of a liquid-air interface between air and the serum or plasma portion, a location of a serum-gel interface between the serum or plasma portion and the gel separator, if the gel separator is used, a location of a serum-blood interface between the serum or plasma portion and the settled blood portion, a location of a blood-gel interface between the settled blood portion and the gel separator, if the gel separator is used, a volume and/or a depth of the serum or plasma portion, or a volume and/or a depth of the settled blood portion.

According to another aspect, a quality check module adapted to quantify a specimen is provided. The quality check module includes a plurality of cameras configured to capture images of the specimen at multiple spectra having different nominal wavelengths, multiple exposures, and from different viewpoints, a computer configured and operable to: select of optimally-exposed pixels from the images at different exposures at each of the multiple spectra to generate optimally-exposed image data for each of the multiple spectra, classify the specimen into various class types comprising one or more of serum or plasma portion, settled blood portion, gel separator, if present, air, tube, label, or cap, and quantify the specimen by determining one or more of: a location of a liquid-air interface between the air and the serum or plasma portion, a location of a serum-blood interface between the serum or plasma portion and the settled blood portion, a location of a serum-gel interface between the serum or plasma portion and the gel separator, if used, a location of a blood-gel interface between the settled blood portion and the gel separator, if used, a volume and/or a depth of the serum or plasma portion, or a volume and/or a depth of the settled blood portion.

In yet another aspect, a specimen testing apparatus is provided. The specimen testing apparatus includes a track, and a quality check module on the track, the quality check module including: a plurality of cameras configured to capture images of the specimen at multiple spectra having different nominal wavelengths, at multiple different exposures, and from different viewpoints, and a computer configured and operable to: select optimally-exposed pixels from the images at the multiple different exposures at each of the multiple spectra to generate optimally-exposed image data for each of the multiple spectra, classify the specimen into various class types comprising one or more of serum or plasma portion, settled blood portion, gel separator, if a gel separator is used, air, tube, label, or cap, and quantify the specimen by determining one or more of: a location of a liquid-air interface between the air and the serum or plasma portion, a location of a serum-blood interface between the serum or plasma portion and the settled blood portion, a location of a serum-gel interface between the serum or plasma portion and the gel separator, if the gel separator is used, a location of a blood-gel interface between the settled blood portion and the gel separator, if the gel separator is used, a volume and/or a depth of the serum or plasma portion, or a volume and/or a depth of the settled blood portion.

In accordance with another aspect, a Monte Carlo simulation method of quantifying a specimen contained within a specimen container is provided. The method includes providing a specimen contained in a specimen container at an imaging location, capturing an image of the specimen, determining regions of the specimen including at least a serum or plasma portion and settled blood portion, drawing level hypotheses from a multi-variate level model, mapping level hypotheses to image space, integrating confidences within the regions, maximizing confidences within each of the regions, and selecting level hypotheses that maximizes confidences.

Still other aspects, features, and advantages of the present invention may be readily apparent from the following description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The invention is to cover all modifications, equivalents, and alternatives falling within the scope of the appended claims.

BRIEF DESCRIPTION OF THE DRAWINGS

The drawings, described below, are for illustrative purposes only and are not necessarily drawn to scale. The drawings are not intended to limit the scope of the invention in any way.

DESCRIPTION

Figure 1:
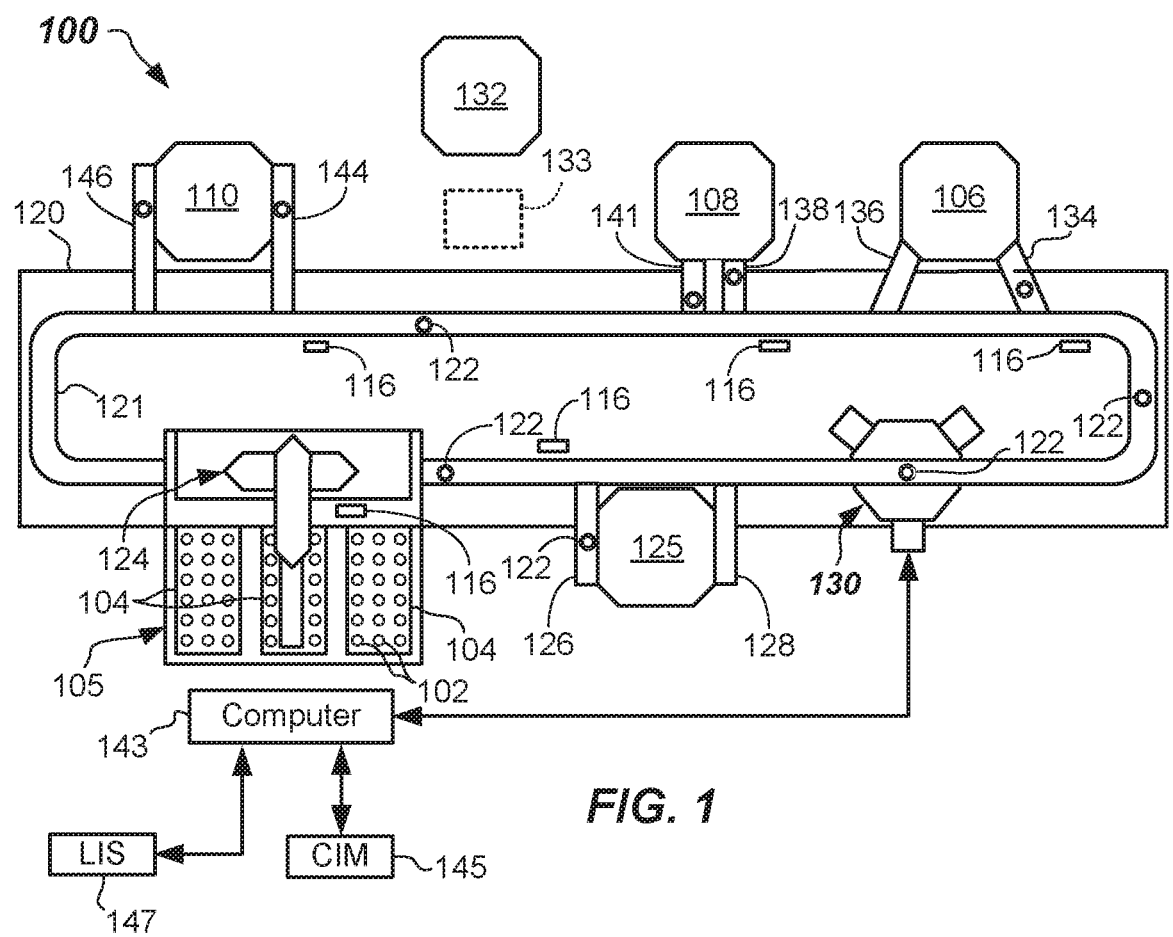
FIG. 1 illustrates a top schematic view of a specimen testing apparatus including one or more quality check modules and one or more analyzers according to one or more embodiments.

In a first broad aspect, embodiments of the present invention provide methods and apparatus to quantify one or more dimensional characteristics of a specimen. "Dimensional characteristics," as used herein, shall mean any dimension of the specimen as a whole, any dimension of a component making up the specimen, such as dimensions of the serum or plasma portion, dimensions of the settled blood portion, dimensions of a gel separator (if used), as well as volumes and/or depths of one or more of these components. More precisely knowing the dimensional characteristics of one or more components of the specimen may be used to properly guide the positioning of the probe (otherwise referred to as a "pipette") within the specimen container during an aspiration sequence so that the probe does not become clogged or contaminated by aspirating settled blood portion or gel separator (if used), and may minimize aspirating air. Furthermore, being able to accurately determine an amount of the serum or plasma portion that is available allows more complete use of that portion, and allows for a pre-check of verification that there will be a sufficient amount of serum or plasma portion present in the specimen container in order to carry out tests when multiple tests are ordered on a particular specimen. Accurately knowing the dimensional characteristics of the serum or plasma portion and the settled blood portion also enables generation of a ratio there between.

The specimen, as described herein, may be collected in a specimen container, such as a blood collection tube and includes a settled blood portion and a serum and plasma portion after separation (e.g., fractionation using centrifugation). The settled blood portion is made up blood cells such as white blood cells (leukocytes), red blood cells (erythrocytes) and platelets (thrombocytes), which are aggregated and separated from the serum or plasma portion. Settled blood portion is generally found at the bottom part of the specimen container. The serum or plasma portion is the liquid component of blood, which is not part of the settled blood portion. It is generally found above the settled blood portion. Plasma and serum differ primarily in the content of coagulating components, primarily fibrinogen. Plasma is the un-clotted liquid, whereas serum refers to blood plasma that has been allowed to clot, either under the influence of endogenous enzymes or exogenous components. In some specimen containers, a gel separator (e.g. plug) may be used, which positions itself between the settled blood portion and the serum or plasma portion during fractionation. It serves as a barrier between the two portions.

In accordance with one or more embodiments, the specimen quantification method may be carried out as a pre-analytical testing method. For example, in one or more embodiments, the specimen quantification method may be carried out prior to the specimen being characterized for the presence of an interferent, or prior to be subjected to routine analysis on an analyzer. In particular, one or more embodiments of the present invention provides for dimensional quantification of a specimen as a prerequisite for further pre-analytical testing. The dimensional quantification of the specimen may be determined at a quality check module. The quality check module may include multiple cameras arranged to provide images of the specimen container and the contained specimen from different lateral viewpoints.

In particular, the dimensional quantification method involves quantification of the serum or plasma portion and possibly other components of the specimen (e.g., settled blood portion) and may be carried out using high dynamic range (HDR) image processing. According to the method, the location of the interfaces of the serum or plasma portion (e.g., the liquid-air interface, the serum-blood interface, or the serum-gel interface) may be very accurately determined using HDR image processing.

After the quantification method has determined the physical dimensional characteristics of the specimen, the generated HDR data sets may be used to determine further information about the specimen, such as if any artifacts (e.g., clot, bubble, foam) are present in the serum or plasma portion, and/or to determine a presence of an interferent, such as hemolysis, icterus, and/or lipemia (hereinafter "HIL"). If the serum or plasma portion is found to contain an artifact, or one or more of HIL, the specimen may be subjected to further processing. For example, an identified clot, bubble, or foam may be taken to another station for manual removal of the clot, bubble, or foam by an operator, or for further processing or characterization for HIL. After such further processing, the specimen may be allowed, in some embodiments, to continue on and undergo routine analysis by the one or more analyzers. If the pre-screening finds that the specimen is normal, then the specimen may be directly routed to undergo routine analysis by one or more analyzers.

In some embodiments, a quality check module is configured to carry out the dimensional quantification method. The quality check module may be provided as part of a laboratory automation system (LAS) where a track transports the specimen to the one or more analyzers, and the quality check module may be provided on the track. In a specific embodiment, the quality check module is provided on the track, such as at a loading station or other position of the track, so that the specimen may be dimensionally quantified on the track.

The quantification method including HDR data processing may include capturing multiple images at the quality check module at multiple exposures (e.g., exposure times) and while illuminated by multiple spectra having different nominal wavelengths. The images may be obtained using a plurality of cameras arranged to capture the images from different viewpoints. Taking the one or more images at multiple spectra (e.g., colors) may be accomplished while using different light sources for illumination. For example, white light sources, red light sources, green light sources, blue light sources, near-infra red light sources, or UV light sources may be used.

Images at multiple exposures for each spectra (or wavelength range) may be obtained by the quality check module. For example, 4-8 or more images at different exposures may be obtained at each spectra (or wavelength range). The exposure may vary based on the lighting intensity and camera features.

Further details of the inventive specimen dimensional quantification method, quality check module, and specimen testing system including the quality check module will be further described with reference to FIGS. 1-8 herein.

Figure 2:
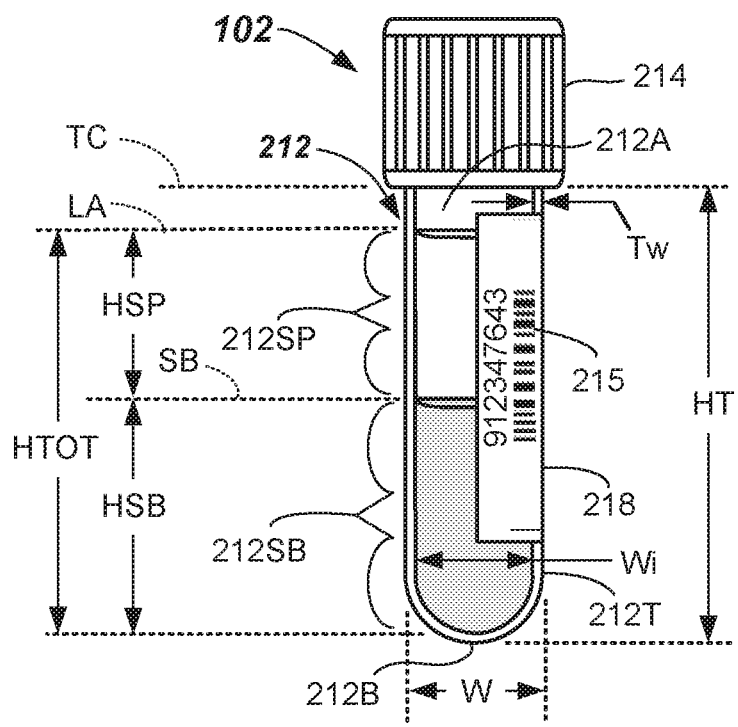
FIG. 2 illustrates a side view of a labeled specimen container including a specimen, which may be quantified by using a specimen quantification method according to one or more embodiments.
Figure 3:
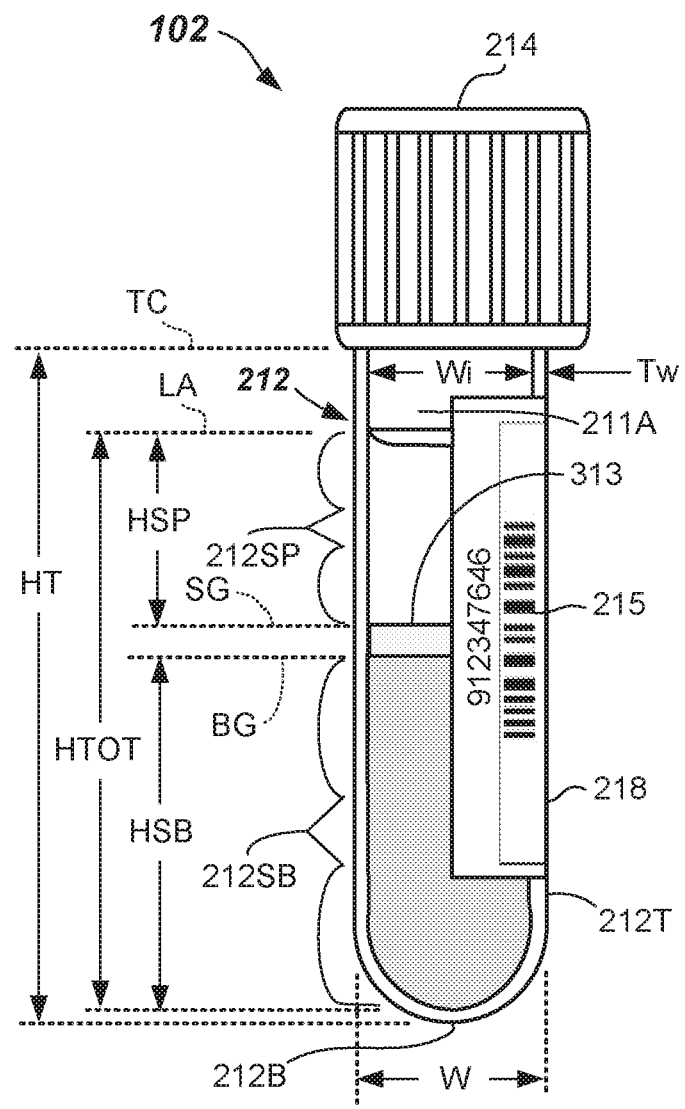
FIG. 3 illustrates a side view of a labeled specimen container including a specimen and a gel separator, which may be quantified by a specimen quantification method according to one or more embodiments.

FIG. 1 shows a specimen testing apparatus 100 capable of automatically processing multiple ones of the specimen containers 102 (e.g., specimen collection tubes—see FIGS. 2 and 3). The specimen containers 102 may be contained in one or more racks 104 at a loading area 105 prior to transportation to, and analysis by, one or more analyzers (e.g., first, second, and third analyzer 106, 108, 110, respectively, arranged about the specimen testing apparatus 100). It should be apparent that more or less numbers of analyzers can be used. The analyzers may be any combination of clinical chemistry analyzers and/or assaying instruments, or the like. The specimen containers 102 may be any generally transparent or translucent container, such as a blood collection tube, test tube, sample cup, cuvette, or other generally clear glass or plastic container. Other suitable containers may be used.

Typically, specimens 212 (FIGS. 2 and 3) to be automatically processed may be provided to the specimen testing apparatus 100 in the specimen containers 102, which may be capped with a cap 214 (FIGS. 2 and 3—otherwise referred to as a "stopper"). The caps 214 may have different shapes and/or colors (e.g., red, royal blue, light blue, green, grey, tan, yellow, or combinations), which may have meaning in terms of the test the specimen container 102 is used for, the type of additive in the specimen container 102, or the like. Other colors may be used.

Each of the specimen containers 102 may be provided with identification information 215 (i.e., indicia), such as a barcode, alphabetic, numeric, alphanumeric, or combinations thereof that may be machine readable at various locations about the specimen testing apparatus 100. The identification information 215 may indicate, or may otherwise be correlated, via a Laboratory Information System (LIS) 147, to a patient's identification as well as tests to be accomplished upon the specimen 212, or other information, for example. Such identification information 215 may be generally provided on a label 218 adhered to, or otherwise provided on the side of, the specimen container 102. The label 218 generally does not extend all the way around the specimen container 102, or all along a length of the specimen container 102. In some embodiments multiple labels 218 may be adhered, and may slightly overlap. Accordingly, although the label 218 may occlude viewing some portions of the specimen 212, some other portions of the specimen 212 may still be viewable from certain viewpoints. Embodiment of the present invention may eliminate rotation of the specimen container (as in the prior art) for characterization. In some embodiments, the racks 104 may have additional identification information thereon, such as barcodes.

The specimen 212 may include a serum or plasma portion 212SP and a settled blood portion 212SB contained within the tube 212T. Air 212A may be provided above the serum and plasma portion 212SP and the line or demarcation between them is defined herein as the liquid-air interface (LA). The line of demarcation between the serum or plasma portion 212SP and the settled blood portion 212SB is defined herein as the serum-blood interface (SB) as is shown in FIG. 2. The interface between the air 212A and the cap 214 is referred to herein as the tube-cap interface (TC). The height of the serum or plasma portion 212SP is (HSP) and is defined as the height from the top of the serum or plasma portion 212SP from the top of the settled blood portion 212SB, i.e., from LA to SB in FIG. 2. The height of the settled blood portion 212SB is (HSB) and is defined as the height from the bottom of the settled blood portion 212SB to the top of the settled blood portion 212SB at SB in FIG. 2. HTOT in FIG. 2 is the total height of the specimen 212 and HTOT=HSP+HSB.

In cases where a gel separator 313 is used (see FIG. 3), the height of the serum or plasma portion 212SP is (HSP) and is defined as the height from the top of the serum or plasma portion 212SP at LA to the top of the gel separator 313 at SG, i.e., from LA to SG in FIG. 3. The height of the settled blood portion 212SB is (HSB) and is defined as the height from the bottom of the settled blood portion 212SB to the bottom of the gel separator 313 at BG in FIG. 3. HTOT in FIG. 3 is the total height of the specimen 212 and HTOT=HSP+HSB+the height of the gel separator 313. In each case, the wall thickness is Tw, the outer width is W and the inner width of the specimen container 102 is Wi. The height of the tube (HT) is defined as the height from the bottom-most part of the tube 212T to the bottom of the cap 214.

In more detail, specimen testing apparatus 100 may include a base 120 (e.g., a frame or other structure) upon which a track 121 may be mounted or supported. The track 121 may be a railed track (e.g., a mono rail track or a multiple rail track), a collection of conveyor belts, conveyor chains, moveable platforms, or any other suitable type of conveyance mechanism. Track 121 may be circular, serpentine, or any other suitable shape. Track 121 may be a closed track (e.g., endless track) in some embodiments. Track 121 may, in operation, transport individual ones of the specimen containers 102 to locations spaced about the track 121 while residing in carriers 122.

Carriers 122 may be passive, non-motored pucks that may be configured to carry a single specimen container 102 on the track 121, or optionally an automated carrier including an onboard drive motor, such as a linear motor that is programmed to move about the track 121 and stop at pre-programmed locations around the track 121. Carriers 122 may each include a holder 122H (FIGS. 4A-4D) configured to hold the specimen container 102 in a defined upright position. The holder 122H may include any suitable construction, and may include a plurality of fingers or leaf springs that secure the specimen container 102 in the carrier 122, but are laterally moveable or flexible to allow for accommodation of different sizes of specimen container 102 to be received therein. In some embodiments, carriers 122 may exit from the loading area 105 having one or more racks 104 staged thereat. In some embodiments, loading area 105 may serve a dual function of allowing offloading of the specimen containers 102 from the carriers 122 after the analysis is completed. Otherwise, an offloading lane may be provided elsewhere on the track 121.

A robot 124 may be provided at the loading area 105 and may be configured to grasp the specimen containers 102 located at the one or more racks 104 and load the specimen containers 102 onto the carriers 122, such as on an input lane of the track 121 or elsewhere on the track 121. Robot 124 may also be configured to remove specimen containers 102 from the carriers 122 upon completion of the analysis. The robot 124 including one or more (e.g., least two) robot arms or components capable of X and Z, Y and Z, X, Y, and Z, r and theta, or r, theta, and Z motion. Robot 124 may be a gantry robot, an articulated robot, an R-theta robot, or other suitable robot wherein the robot 124 may be equipped with robotic gripper fingers sized to pick up and place the specimen containers 102.

Upon being loaded onto track 121, the specimen containers 102 carried by carriers 122 may progress to a centrifuge 125 (e.g., an automated centrifuge) that may be configured to carry out fractionation of the specimen 212. Carriers 122 carrying specimen containers 102 may be diverted to the centrifuge 125 by inflow lane 126 or other suitable robot. After being centrifuged, the specimen containers 102 may exit on outflow lane 128, or otherwise be removed by a robot, and continue on the track 121. In the depicted embodiment, the specimen container 102 in carrier 122 may next be transported to a quality check module 130 to be further described herein with reference to FIGS. 4A and 4D.

The quality check module 130 is configured and adapted for quantification of the specimen 212 contained in the specimen container 102. Quantification of the specimen 212 may take place at the quality check module 130 and may include determination of HSP, HSB, HTOT, and determination of a location of SB, LA, SG, and/or BG). The quality check module 130 may also be configured for determining a presence of an interferent, such as one or more of hemolysis (H), icterus (I), and/or lipemia (L) contained in a specimen 212 to be processed by the specimen testing apparatus 100. In some embodiments, the specimen 212 may also be tested for the presence of an artifact (e.g., clot, bubble, or foam) at the quality check module 130. In some embodiments, quantification of the physical attributes of the specimen container 102 may take place at the quality check module 130 such as determining HT, cap color, cap type, TC, and tube width (W).

Once the specimen is quantified, and the specimen 212 and/or specimen container 102 may be pre-screened for presence of an interferent, for one or more artifacts, or for further characterization of the specimen container 102, then the specimen 212 may be forwarded to be analyzed in the one or more analyzers (e.g., analyzers 106, 108, and/or 110) before returning each specimen container 102 to the loading area 105 for offloading.

Additionally, a remote station 132 may be provided on the automated specimen testing apparatus 100 even though the remote station 132 is not directly linked to the track 121. For instance, an independent robot 133 (shown dotted) may carry specimen containers 102 containing specimens 212 to the remote station 132 and return them after testing/processing. Optionally, the specimen containers 102 may be manually removed and returned. Remote station 132 may be used to test for certain constituents, such as a hemolysis level, or may be used for further processing, such as to lower a lipemia level through one or more additions, or to remove a clot, bubble or foam, for example. Other testing or processing may be accomplished on remote station 132. Further, additional stations (not shown) may be arranged around the track 121, such as a de-capping station, aliquot preparation, or the like.

The specimen testing apparatus 100 may include a number of sensors 116 at one or more locations around the track 121. Sensors 116 may be used to detect a location of specimen containers 102 along the track 121 by means of reading the identification information 215 (FIG. 2) placed on the specimen container 102, or like information (not shown) that may be provided on each carrier 122. In some embodiments, a distinct RFID chip may be embedded in each carrier 122 and conventional RFID reader system may be employed in the tracking operation, for example. Other means for tracking the location may be used, such as proximity sensors. All of the sensors 116 may interface with the computer 143 so that the location of each specimen container 102 may be appropriately known at all times.

Centrifuge 125 and each of the analyzers 106, 108, 110 may be generally equipped with robotic mechanisms and/or inflow lanes (e.g., inflow lanes 126, 134, 138, 144) configured to remove carriers 122 from the track 121, and robotic mechanisms and/or outflow lanes (e.g., outflow lanes 128, 136, 141 and 146) configured to reenter carriers 122 to the track 121.

Specimen testing apparatus 100 may be controlled by the computer 143, which may be a microprocessor-based central processing unit CPU, having a suitable memory and suitable conditioning electronics, drivers, and software for operating the various system components. Computer 143 may be housed as part of, or separate from, the base 120 of the specimen testing apparatus 100. The computer 143 may operate to control, via programmed instructions, movement of the carriers 122 to and from the loading area 105, motion about the track 121, motion to and from the centrifuge 125. Computer 143 or a separate computer may control operation of the centrifuge 125, motion to and from the quality check module 130 as well as operation of the quality check module 130, and motion to and from each analyzer 106, 108, 110 as well as operation of each analyzer 106, 108, 110 for carrying out the various types of testing (e.g., assay or clinical chemistry).

For all but the quality check module 130, the computer 143 may control the specimen testing apparatus 100 according to software, firmware, and/or hardware commands or circuits such as those used on the Dimension® clinical chemistry analyzer sold by Siemens Healthcare Diagnostics Inc. of Tarrytown, N.Y., and such control is typical to those skilled in the art of computer-based electromechanical control programming and will not be further described herein. However, other suitable systems for controlling the specimen testing apparatus 100 may be used. The control of the quality check module 130 may also be provided by the computer 143, but according to an inventive model-based method, as will be described in detail herein.

Embodiments of the present invention may be implemented using a computer interface module (CIM) 145 that allows for a user to easily and quickly access a variety of control screens and status display screens. These control and status screens may describe some or all aspects of a plurality of interrelated automated devices used for preparation and analysis of specimens 212. The CIM 145 may be employed to provide information about the operational status of a plurality of interrelated automated devices as well as information describing the location of any specimen 212 as well as a status of tests to be performed on, or being performed on, the specimen 212. The CIM 145 is thus adapted to facilitate interactions between an operator and the specimen testing apparatus 100. The CI M 145 may include a display screen adapted to display a menu including icons, scroll bars, boxes, and buttons through which the operator may interface with the specimen testing apparatus 100.

In FIGS. 2 and 3, specimen containers 102 including specimen 212 are shown. FIG. 2 illustrates a specimen 212 including the serum or plasma portion 212SP and the settled blood portion 212SB, without a gel separator. FIG. 3 illustrates a specimen 212 including the serum or plasma portion 212SP and the settled blood portion 212SB with a gel separator 313. Pre-screening the specimen 212 in accordance with an aspect of the invention allows accurate quantification of the relative amounts of the serum or plasma portion 212SP and the settled blood portion 212SB, but also the physical locations of LA, SB, and SG. Quantification ensures that the specimen 212 can be stopped from progressing on to the one or more analyzers 106, 108, 110, if there is insufficient amount of serum or plasma portion 212SP available to carry out the ordered tests. In this way, inaccurate test results may be avoided.

Advantageously, the ability to accurately quantify the location of LA and SB or SG may minimize not only the possibility of aspirating air, but also minimize the possibility of aspirating either settled blood portion 212SB or gel separator 313, if used. Thus, clogging and contamination of the specimen aspirating probe used to aspirate serum or plasma portion at the analyzers 106, 108, 110 may be avoided or minimized in some embodiments.

Figure 4A:
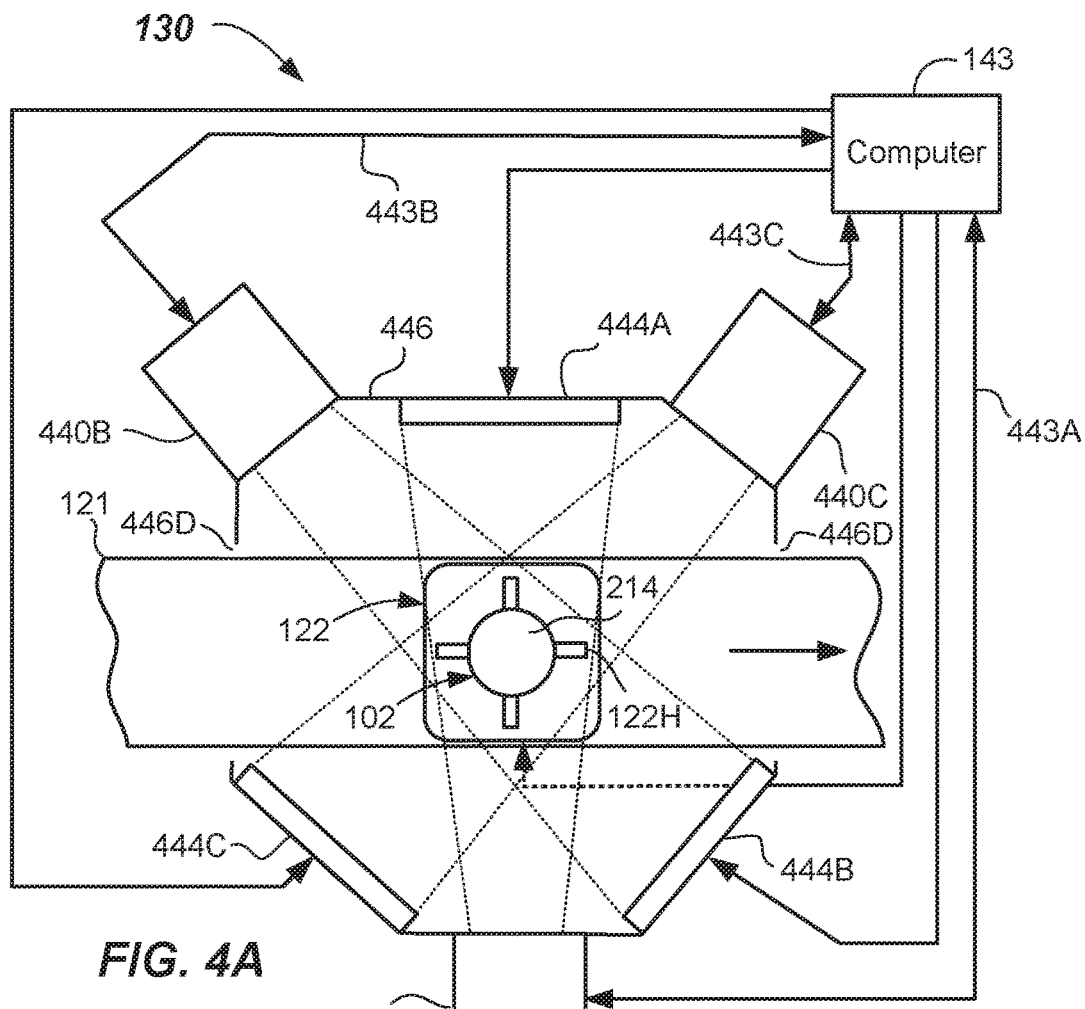
FIG. 4A illustrates a schematic top view of a quality check module configured to capture and analyze multiple images in order to quantify a specimen according to one or more embodiments.
Figure 4B:
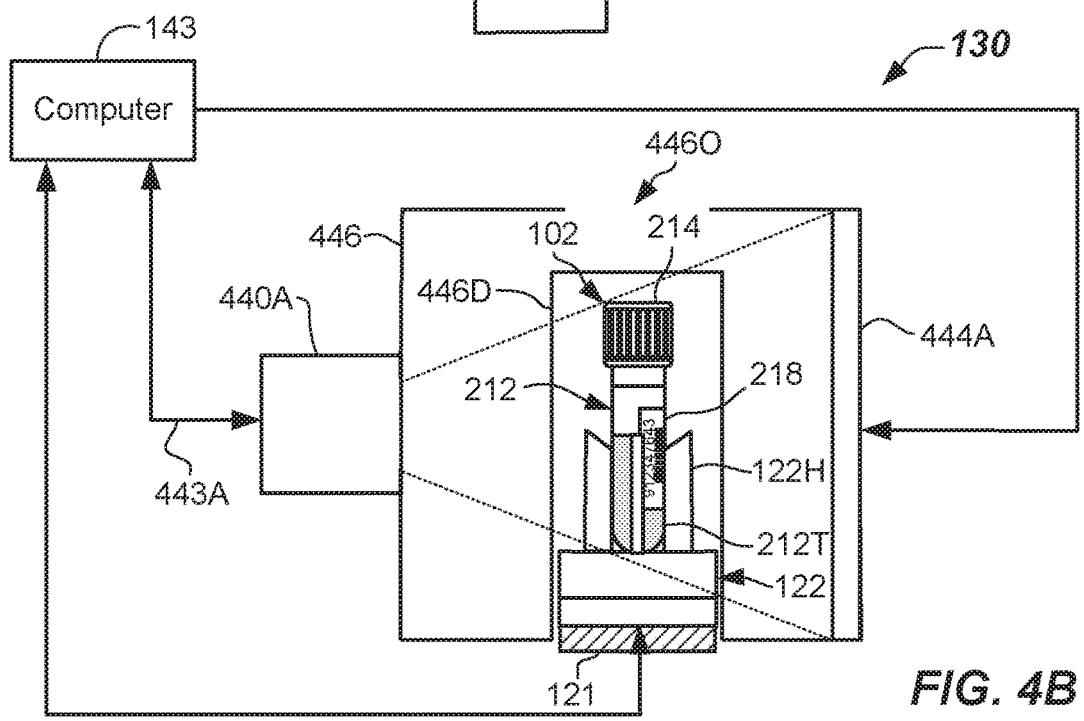
FIG. 4B illustrates a schematic side view of the quality check module of FIG. 4A according to one or more embodiments.

With reference to FIGS. 4A-4B, a first embodiment of a quality check module 130 is shown and described. Quality check module 130 may be configured and adapted to automatically quantify the specimen (e.g., quantity the serum or plasma portion 212SP, the settled blood portion 212SB, or both) prior to analysis by the one or more analyzers 106, 108, 110. Pre-screening in this manner allows for precise aspiration probe positioning, and determination that a sufficient amount (e.g., volume or depth) of the liquid portion (e.g., serum or plasma portion 212SP of the specimen 212) is available, thus avoiding wasting valuable analyzer resources or aspirating air, settled blood portion 212SB or gel separator 313 (if used).

In addition to the specimen quantification method wherein one or more of a physical location of LA, SB and/or SG, and/or determination of HSP, HSB, and/or HTOT, and/or a volume or depth of the serum or plasma portion (VSP) and/or a volume or depth of the settled blood portion (VSB) is quantified, other detection methods may take place on the specimen 212 contained in the specimen container 102 at the quality check module 130. For example, in some embodiments, an interferent detection method may determine the presence or absence of an interferent (e.g., H, I, and/or L). An artifact detection method may determine the presence or absence of an artifact (e.g., clot, bubble, or foam). Furthermore, the quality check module 130 may be used to quantify the specimen container 102, i.e., quantify certain physical dimensional characteristics of the specimen container 102, such as the location of TC, HT, and/or W of the specimen container 102, and/or a color of and/or type of the cap 214.

Now referring to FIGS. 1, 4A and 4B, a first embodiment of a quality check module 130 may include multiple cameras 440A-440C. Three cameras 440A-440C are shown, but two or more, three or more, or even four or more cameras can be used. Cameras 440A-440C may be conventional digital cameras capable of capturing a digital image (i.e., a pixelated image), charged coupled devices (CCD), an array of photodetectors, one or more CMOS sensors, or the like. For example, the three cameras 440A, 440B, 440C are illustrated in FIG. 4A and are configured to capture digital images from three different viewpoints. Each camera 440A, 440B, 440C may be a device capable of capturing a digital pixelated image having an image size that may be about 2560 pixels×694 pixels in one embodiment, and about 1280 pixels×384 pixels in another embodiment. Other pixel densities may be used. Each camera 440A-440C may be configured and operable to capture lateral images of at least a portion of the specimen container 102, and at least a portion of the specimen 212. For example, the cameras 440A-440C may capture a part of the label 218 or cap 214 and part of the tube 212T. Eventually, from the multiple images, a composite model of the specimen 212 in the specimen container 102 can be developed. The composite model may be a 3D model in some embodiments, and may be used to make final determinations or to confirm determinations made by the individual cameras about the specimen 212.

In the embodiment shown, the plurality of cameras 440A-440C are arranged around the specimen 212 and configured to capture lateral images from multiple viewpoints. The viewpoints may be spaced so that they are approximately equally spaced from one another, such as about 120 degrees from one another, as shown, when three cameras 440A, 440B, 440C are used. As depicted, the cameras 440A-440C may be arranged around the track 121. Other arrangements and spacing of the plurality of cameras 440A-440C may be used. In this way, the images of the specimen 212 in the specimen container 102 may be taken, while the specimen container 102 is residing in the carrier 122, but without rotating the specimen container 102. The images may overlap slightly.

In one or more embodiments, the carriers 122 may be stopped at a pre-determined location in the quality check module 130, such as at a point where normal vectors from each of the cameras 440A-440C intersect. In some embodiments, a gate may be provided to stop the carriers 122 at the pre-determined location, so that good quality images may be captured. In other embodiments, the carriers 122 may include a linear motor configured to stop the carrier 122 at desired locations, as programmed. In an embodiment where there is a gate at the quality check module 130, one or more sensors (like sensors 116) may be used to determine the presence of a carrier 122 at the quality check module 130.

The cameras 440A-440C may be provided in close proximity to and trained or focused to capture an image window, i.e., an area including an expected location of the specimen container 102, wherein the specimen container 102 may be stopped so that it is approximately located in a center of the view window. As configured, the cameras 440A-440C can take images that include portions of the serum or plasma portion 212SP, portions of the settled blood portion 212SB, and some or all of the cap 214, and possibly the bottom-most portion of the tube 212T or a reference datum. Within the images, one or more reference datum may be present. The reference datum may aid in quantification of the specimen 212. Reference datum may be TC or the bottom-most portion of the specimen container 102, or a mark in a known location somewhere on the specimen container 102, for example.

In operation, each image may be triggered and captured responsive to a triggering signal provided in communication lines 443A-443C that may be sent by the computer 143. Each of the captured images may be processed according to one or more embodiments of the quantification method provided herein. In particular, HDR processing may be used to capture and process the images in order to quantify the specimen 212.

In more detail, multiple images are captured of the specimen 212 (e.g., the specimen 212 separated by fractionation) at the quality check module 130 at multiple different exposures (e.g., exposure times), while illuminated by different spectra having different nominal wavelengths, and at different viewpoints. For example, each camera 440A-440C may take 4-8 or more images at different exposures times at one or more spectra (or one or more wavelength ranges, such as white light). The images at the different exposures for each spectrum may be taken simultaneously for all cameras 440A-440C.

Figure 4C:
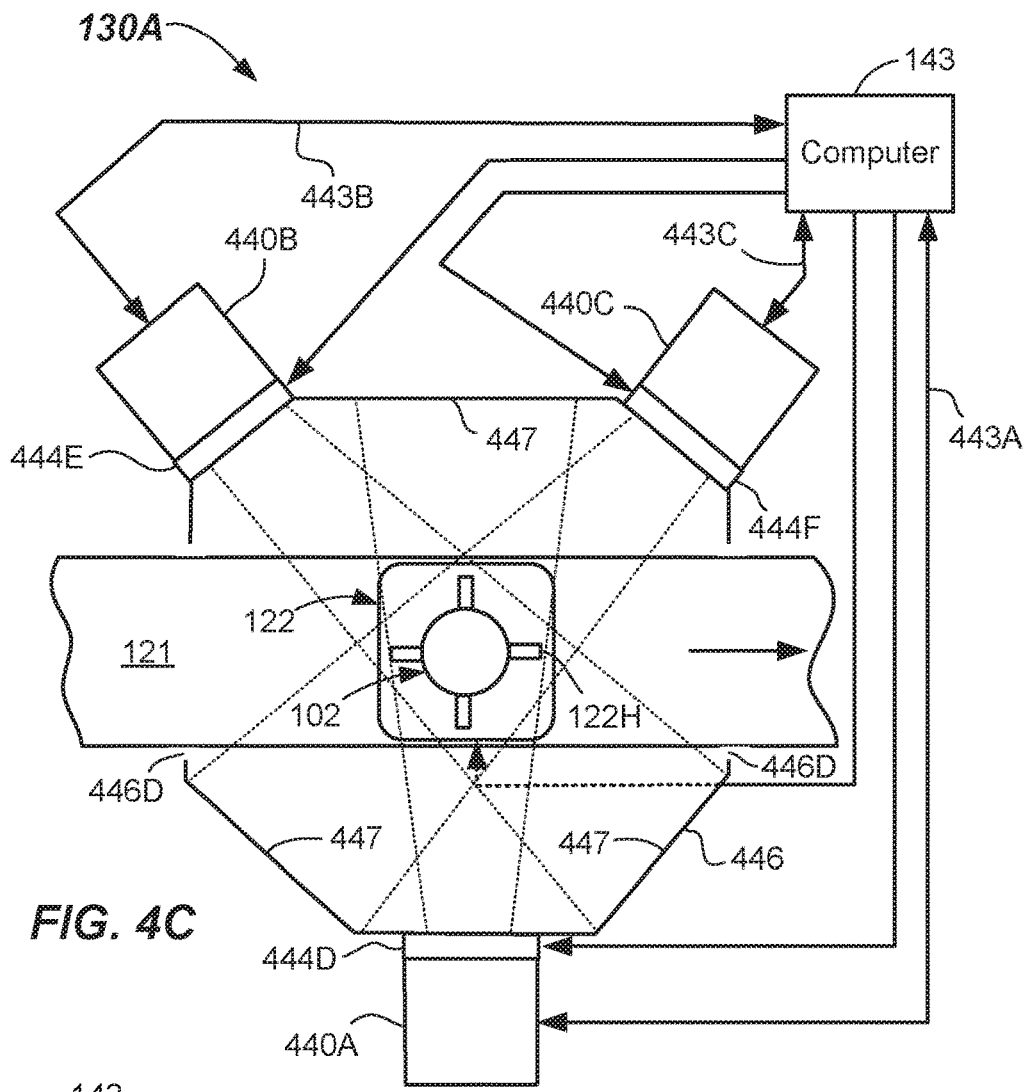
FIG. 4C illustrates a schematic top view of a quality check module configured to capture and analyze multiple images in order to quantify a specimen according to one or more embodiments.
Figure 4D:
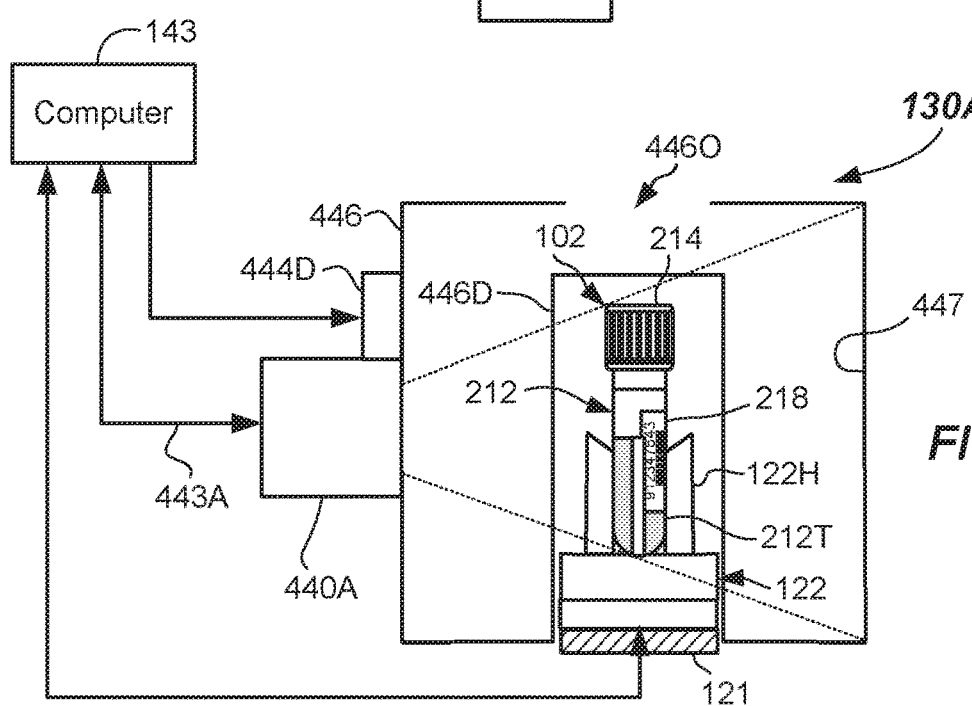
FIG. 4D illustrates a schematic side view of the quality check module of FIG. 4C according to one or more embodiments.

In one embodiment, the multiple wavelength images may be accomplished by illuminating the specimen container 102 and specimen 212 using different colored light sources 444A-444C. The light sources 444A-444C may back light the specimen container 102 (as shown in FIGS. 4A-4B) in a first embodiment. Optionally, light sources 444D-444F may front light the specimen container 102, such as by being arranged above, below, or to the side of the respective cameras 440A-440C, or be elsewhere located as shown in FIGS. 4C-4D. A light diffuser and/or light filter may be used in conjunction with the light sources 444A-444C or 444D-444F in some embodiments.

For example, to capture images with the first spectra, three red light sources (nominal wavelength of about 450 nm with spectral range of about +/−35 nm) may be used to illuminate the specimen 212 from three laterally-spaced locations. The red illumination by the light sources 444A-

444C may occur as the multiple images (e.g., 4-8 or more images) at different exposure times are captured by each camera 440A-440C. In some embodiments, the exposure times may be between about 1 ms and 256 ms. For example, exposure times of 8 ms, 32 ms, 128 ms, and 156 ms may be used. Other exposure times may be used.

In each embodiment, the quality check module 130, 130A may include a housing 446 that may at least partially surround or cover the track 121, and the specimen container 102 may be located inside the housing 446 during the image taking phase so that external lighting is minimized. Housing 446 may include one or more doors 446D to allow the carriers 122 to enter into and/or exit from the housing 446. In some embodiments, the ceiling may include an opening 446O to allow a specimen container 102 to be loaded into the carrier 122 by a robot including robot gripper fingers from above. In the case where front lighting is used for illumination, the quality check module 130A may include backstop walls 447 to provide improved image contrast. Backstop walls 447 may be any suitable color other than the expected range of color of the specimen 212. In some embodiments, a black-colored material may be used.

Once the red illuminated images are captured in the embodiment of FIGS. 4A-4B, the red light sources 444A-444C may be turned off and another spectra of light, for example, green light sources 444A-444C may be turned on (nominal wavelength of about 560 nm with spectral range of about +/−35 nm), and multiple images (e.g., 4-8 or more images) at different exposure times may be captured at that wavelength by each camera 440A-440C arranged at the different viewpoints. This may be repeated with blue light sources 444A-444C (nominal wavelength of about 635 nm with spectral range of about +/−35 nm) for each camera 440A-440C. More or less wavelengths or different nominal wavelengths than RGB may be used. The different wavelength light sources 444A-444C may be accomplished via use of exchangeable filters, for example, or banks of different colored light sources that can be selectively turned on and off, for example. Other means for generating different spectra (colored) lighting may be used.

In the optional embodiment, as best shown in FIGS. 4C and 4D, the specimen container 102 may include front lighting in the quality check module 130A, such as by including light sources 444D, 444E, and 444F arranged adjacent to the cameras 440A-440C, i.e., above, below, to a side, or combinations, but on the same side of the specimen container 102 as the respective cameras 440A-440C. In this optional embodiment, the cameras 440A-440C may be digital color cameras having RGB peaks of approximately 635 nm, 560 nm, and 450 nm, respectively, but wherein each of the RGB colors has a relatively wider wavelength range as compared to the discreet light sources used in the above embodiment in conjunction with the monochrome cameras.

In this optional embodiment, the light sources 444D, 444E, and 444F may each be white light sources. For example, the light sources 444D-444F may emit a wavelength range of between about 390 nm to about 700 nm and may be used to illuminate the specimen 212 from multiple lateral locations. Multiple images at different exposure times (e.g., 4-8 or more exposures) may be taken by each camera 440A-440C. Each white-light image taken may be separated into its color components at multiple wavelengths to provide the captured images and multiple wavelengths. For example, computer 143 may separate the taken images into at least three captured wavelengths between about 400 nm and about 700 nm. For example, RGB components at 450 nm, 560 nm, and 635 nm, respectively, may be separated out of the images by the computer 143 to capture the multi-spectral, multi-time exposure captured images. Images may be taken, as before, via signals from the computer 143 in lines 443A-443C.

For each of the above setups, all of these multiple images taken at multiple exposure times for each respective wavelength (e.g., R, G, and B) may be obtained in rapid succession, such that the entire collection of images for the specimen 212 from multiple viewpoints may be obtained in less than about 2 s. For example, four different exposure images for each wavelength at three viewpoints using three cameras 440A, 440B, 440C and back lighting with RGB light sources 444A-444C will result in 4 images×3 colors×3 cameras=36 images, taken is rapid succession. In another example, four different exposure images at three viewpoints using the cameras 440A, 440B, 440C and front lighting with white light sources 444D-444F will result in 4 images×3 cameras=12 images. However, RGB images are then captured by separating the white light images taken by the cameras 440A-440C into the individual RGB components thereof. Thus, after separation, 36 images are also captured. The image data may be stored in memory of the computer 143 and subsequently processed thereby to quantify the specimen 212.

According to the specimen quantification method, the processing of the image data may involve, for example, selection of optimally-exposed pixels from the multiple captured images at the different exposures for each spectra and for each camera 440A-440C, so as to generate optimally-exposed image data for each spectra (e.g., R, G, and B) and for each camera 440A-440C. This is referred to as "image consolidation" herein. For each corresponding pixel, for each of the exposure time images from each camera 440A-440C, pixels exhibiting optimal image intensity are selected from each of the different exposure time images. Optimal image intensity may be defined as pixels that fall within a predetermined intensity range (e.g., intensity of between 180-254 on a scale of 0-255), for example. If more than one pixel in the corresponding locations of two images is determined to be optimally exposed, the higher of the two is selected. The result is a plurality of consolidated color image data sets (e.g., R, G, B) for each camera 440A-440C where all of the pixels are optimally exposed (e.g., one image data set per wavelength (e.g., R, G, and B) and camera. The optimally exposed intensity values for each pixel are then normalized by the exposure time, so that all pixels are normalized regardless of exposure time.

As part of the calibration of the quality check modules 130, 130A, reference images without a specimen container 102 or carrier 122 may be taken. In this way, background may be removed from each image data set leaving only foreground. Reference images for each exposure time and lighting condition (R, G, B, or white light) may be taken by the quality check module 130, 130A before carrying out the specimen quantification method, for example.

For each image data set including optimally-exposed pixels, a characterization process is undertaken to identify the pixels. The pixels may be classified as liquid region (i.e., the serum or plasma portion 212SP of the specimen 212), or as belonging to another class. Identifying the serum or plasma portion 212SP may be based on classifying each the pixels in the optimally-exposed image data. Classification may be based upon a multi-class classifier (e.g., multi-class classifier 515) generated from multiple training sets. The multi-class classifier 515 may comprise a support vector machine (SVM) or a random decision tree, for example. Other means for determining the liquid region may be used.

To carry out the pixel classification in a segmentation phase, first statistical data may be computed for each of the optimally-exposed pixels at the different spectra (e.g., R, G, and B) for each camera 440A-440C. The statistical data may include attributes up to second order, which may include mean values, variation and correlation values. In particular, a covariance matrix may be computed over multi-dimensional data and represents discriminative patterns.

Once generated, the statistical data is presented to, and operated on, by the multi-class classifier 515, which may classify the pixels in the image as belonging to one of a plurality of class labels, such as 1—serum or plasma portion, 2—settled blood portion, 3—gel separator (if used), 4—air, 5—tube, 6—label, 7—cap. Optionally, carrier may also be classified. From this, the pixels making up the liquid region (i.e., the serum and plasma portion 212SP) may be identified.

The multi-class classifier 515 may be any suitable type of supervised classification model that is linear or non-linear. For example, the multi-class classifier 515 may be a support vector machine (SVM) that is either linear or kernel-based. Optionally, the multi-class classifier 515 may be a boosting classifier such as an adaptive boosting classifier (e.g., Ada-Boost, LogitBoost, or the like), any artificial neural network, a tree-based classifier (e.g., decision tree, random decision forests), and logistic regression as a classifier, or the like. A SVM may be particularly effective for classification between liquids and non-liquids, such as found in the analysis of the specimen 212. A SVM is a supervised learning model with associated learning algorithms that analyzes data and recognizes patterns. SVMs are used for classification and regression analysis.

Multiple sets of training examples are used to train the multi-class classifier 515, and then the image data set is operated on multi-class classifier 515 and each pixel is classified. The multi-class classifier 515 may be trained by graphically outlining various regions in a multitude of examples of specimen containers 102 having various specimen conditions, occlusion by label 218, levels of serum or plasma portion 212SP and settled blood portions 212SB, containing gel separator 313 or not, and the like. As many as 500 or more images may be used for training the multi-class classifier 515. Each training image may be outlined manually to identify and teach the multi-class classifier 515 the areas that belong to each class.

An SVM training algorithm builds the multi-class classifier 515 that assigns pixels of any new teaching specimens into one of the classes. The SVM model represents examples as points in space that are mapped so that the examples of the separate classes are divided by a clear gap that is as wide as possible. New pixels from the image data set may be mapped into that same space and predicted to belong to a particular class based on where they fall on the map. In some embodiments, SVMs can efficiently perform a non-linear classification using what is called a kernel trick (e.g., kernel-based SVM classifier), implicitly mapping their inputs into high-dimensional feature spaces. SVM and tree-based classifiers are particularly preferred. Other types of classification models may be used.

The results of the multi-class classifier 515 that are deemed to be of the class serum or plasma portion 212SP and/or settled blood portion 212SB may then be used to quantify the specimen 212. A width (W) of the specimen container 102 may also be determined.

Figure 5:
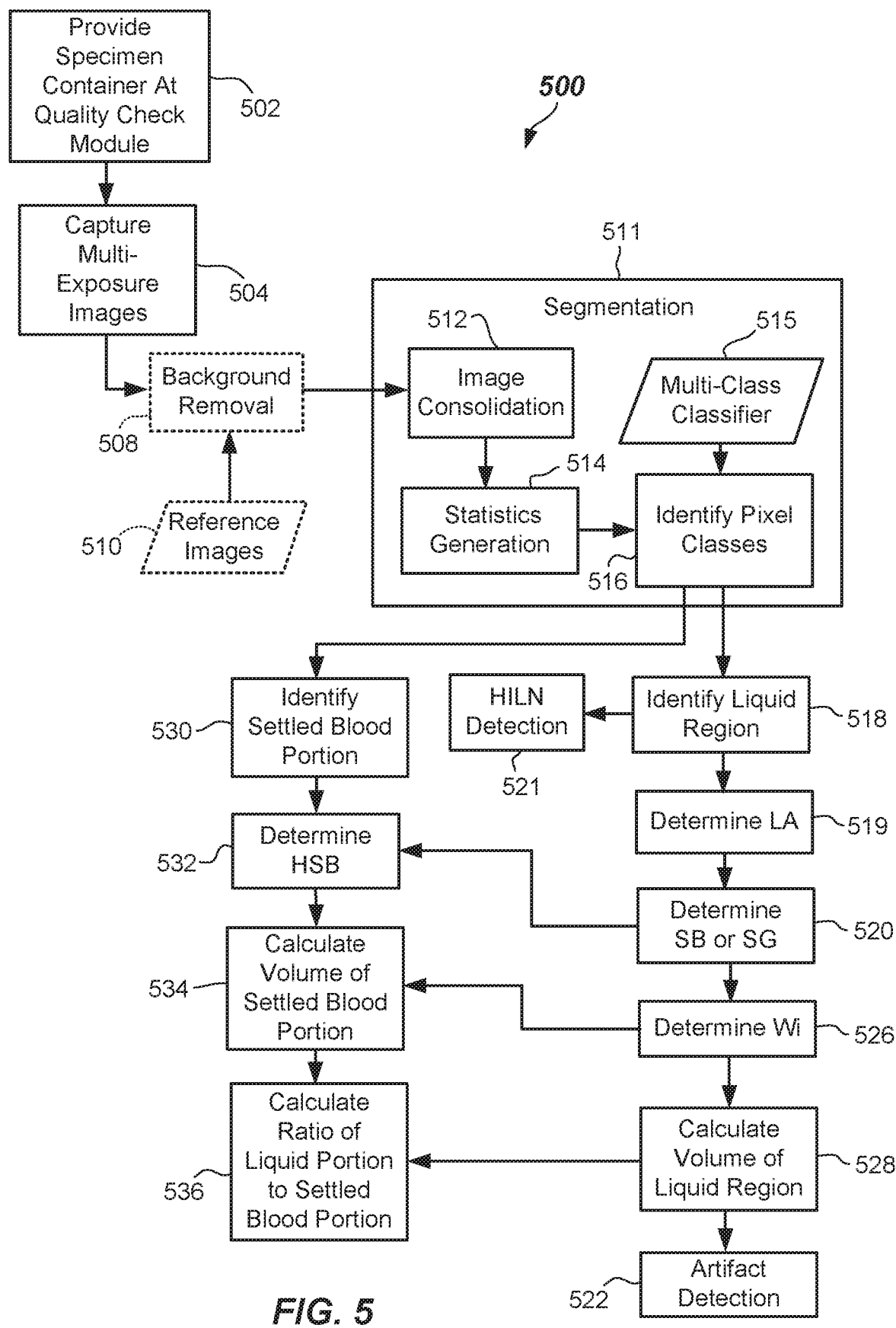
FIG. 5 illustrates a block diagram of components of a quality check module configured to quantify a specimen according to one or more embodiments.

A flow chart of the specimen quantification method according to one or more embodiments is shown in FIG. 5. First, the specimen container 102 including specimen 212, carried by carrier 122, is provided at the quality check module (e.g., quality check module 130 or 130A) in 502. Multiple images are captured at 504; the multiple images being multi-spectral images taken at multiple different exposures and at multiple different spectra and multiple viewpoints, as described above. For quantification, the front lighted setup of quality check module 130A may be used, and the multiple images may be stored in memory of the computer 143. From these images, the background may optionally be subtracted in a background removal phase of 508 to lower computational burden. Background reduction may be accomplished by subtracting reference images previously taken in 510.

After image capture in 504, and optional background removal in 508, segmentation may be undertaken in 511. The segmentation in 511 may include an image consolidation process that is undertaken in 512. During this image consolidation process in 512, the various exposure time images at each spectra (R, G, and B) and for each camera 440A-440C are reviewed pixel by pixel to determine those pixels that have been optimally exposed. For each corresponding pixel location, the best of any optimally-exposed pixel is selected and normalized and included in an optimally-exposed image data set for each spectra and camera 400A-440C. Thus, following image consolidation in 512, there is produced one optimally-exposed image data set for each spectra (R, G, and B) and for each camera 440A-440C. The use of HDR processing may function to enrich the details of the images with respect to reflections and absorption. This may make quantification more precise.

Following image consolidation in 512, or possibly concurrent therewith, a statistics generation process may be undertaken in 514, where statistics are generated for each pixel, such as up to $2^{nd}$ order mean values and/or covariance. This statistical data on the optimally-exposed data sets are then operated on by a multi-class classifier 515 to provide identification of the pixel classes present in the image data sets in 516. For each pixel location, this statistical description is extracted within a small super-pixel patch (e.g. 11×11 pixels). Each super-pixel patch provides a descriptor, which is considered in the training and evaluation process. Typically the classifiers operate on these feature descriptors and use input class labels for training and output class labels during testing. To obtain a class label for each pixel the image data sets are scanned by suitable known scanning techniques.

From this segmentation process of 511, each pixel in a 2D consolidated image data set for each of the cameras 440A-440C is given a classification as belonging to one of the plurality of class types in 516. Class types may be liquid (serum or plasma portion 212SP), settled blood portion 212SB, gel separator 313, air 212A, tube 212T, label 218, or cap 214, for example. From this segmentation information in 511, quantification of the specimen 212 may be determined.

For example, the liquid region (e.g., the serum or plasma portion 212SP) may be identified in 518. This may involve grouping all the pixels from the class—serum or plasma portion 212SP, and then determining a location of the upper interface between liquid (serum or plasma portion 212SP) and air 212A (i.e., LA) in 519. A numerical value for LA in the vertical direction may be calculated by averaging the locations of the uppermost pixels classified as serum or plasma portion 212SP in the 2D consolidated image data set. Any substantial outliers may be rejected and not used in the average. Previously performed pixel space to machine space (e.g., in mm) calibration may be accomplished by any known machine space to image space calibration technique.

Depending on whether a gel separator 313 is used, the quantification method then determines the physical vertical location of SB or SG (if gel separator is used) in 520.

A numerical value for SB or SG may be calculated in 520 by averaging the locations of the lowermost pixels classified as serum or plasma portion 212SP. Again outliers may be ignored. From the locations of LA and SB or SG, the height of the serum or plasma portion (HSP—FIGS. 2 and 3) may be determined via subtraction of the averages. Other means for calculating the height HSP may be used, such as counting the vertical stacks of pixels identified as serum or plasma portion 212SP, averaging the number of pixels, and then converting to machine space, for example.

Quantifying the liquid region (e.g., the serum or plasma portion 212SP) may further include determining the inner width (Wi) of the specimen container 102 in 526. The outer width (W) may be determined in 526 by identifying the pixels classified as tube 212T and subtracting the locations of corresponding ones of the pixels that are located on the outside lateral edges of the tube 212T as measured between LA and SB or SG, and then averaging the subtracted values, for example. Wi may be determined from W by subtracting twice the wall thickness Tw, i.e., Wi=W−2Tw. Tw may be an average wall thickness value used for all specimen containers 102 or may be a specific measured value obtained from a lookup table based upon the tube type determined based upon the determination of the outer width W and the height HT.

From HSP and Wi, the volume of the liquid region VSP (e.g., the serum or plasma portion 212SP) may be determined using Eqn. 1 below in 528.

$$VSP = HSP \times Pi/4\,Wi^2 \qquad \text{Eqn. 1}$$

To quantify the settled blood portion 212SB, the pixels corresponding to the class of settled blood portion 212SB may first be identified in 530. Depending on whether a gel separator 313 is present, height of the settled blood portion HSB may be determined in 532 by locating the lowermost pixel of the settled blood portion 212SB and then subtracting either SB or BG. SB or SG may be determined in 520. A numerical value for SB or BG may be determined by averaging the locations of the uppermost pixels classified as settled blood portion 212SB. Wi may be determined in 526. From HSB and Wi, the volume of the settled blood portion 212SB may be determined in 534 using Eqn. 2 below which includes a subtracted adjustment factor to account for the rounded end of the specimen container.

$$VSB = (HSB \times Pi/4\,Wi^2) - \{½Wi^2 - (Pi/24)Wi^3\} \qquad \text{Eqn. 2}$$

Once VSP and VSB are determined in 528 and 534, the Volume Ratio of liquid portion (e.g., serum or plasma portion 212SP) to settled blood portion 212SB may be calculated in 536, wherein Volume Ratio=$\{VSP/VSB\} \times 100$ (%).

Optionally, the depth levels of the liquid portion (i.e., the serum or plasma portion 212SP) and the settled blood portion 212SB may be determined using a Monte Carlo simulation method. The Monte Carlo simulation method is a class of computational algorithm that is based on repeated random sampling from a given model distribution to obtain a numerical solution. The method relies on generating a plurality of random hypotheses from a multi-variate level model, which then are verified/tested with image measurements such as confidence values generated during an image capture phase. The Monte Carlo simulation method involves deriving hypotheses of the locations of LA, SB, or SG and BG, for example, depending on whether a gel separator 313 is used. In order to apply the Monte Carlo simulation method, a model distribution is required from where random samples are drawn. The model may be a multi-variate model trained with a large amount of annotated training specimens.

During a training phase, landmark-based layer annotations are collected and an estimate of a model is derived from these annotations. For generation we assume the knowledge of two reference landmarks $L=(l_1,l_2)$ in the image i.e. the liquid-air interface LA, and the lowest part 212B of the specimen container 102 e.g. the tip. These are called landmark reference points. Additionally, we assume a landmark annotation of the SG interface between serum and plasma portion 212SP and gel separator 313, and a landmark annotation of the blood-gel interface BG between gel separator 313 and settled blood portions 212SB. In particular, they may be denoted as level points $p=(p_1,p_2)^T$. Landmark-based annotations are sufficient assuming that the photos are captured with an up vector of the camera (e.g., camera 440A) aligned with the gravity vector (which is typically the case in the proposed hardware setup for the quality check modules 130, 130A). FIGS. 2 and 3 show a potential annotation of a specimen image.

In one or more embodiments, the method may normalize the extension of fluid region to a canonical representation. In particular, it is assumed that the fluid levels are perpendicular to the gravity vector, thus the normalization scheme is independent of tilt of the specimen container 102. Furthermore, it is assumed that the height of the fluid HT (computed along the gravity vector) is normalized to a value of one within this canonical representation (based on the two landmark reference points $(l_1,l_2)$). Based on this normalization scheme, normalized ratios for the pair of level points p can be derived for each annotated sample image. Multivariate statistics are derived from a set of annotated training images under consideration of $P=\{p^1, p^2, p^3, \ldots, p^k\}$.

For modeling we assume a multi-variate Gaussian distribution for the two level points, resulting in a mean p and variance/covariance matrix $\Sigma$ in a normalized representation: (1) $\mu=E(P)$ and (2) $\Sigma=E[(P-E(P))(P-E(P))^T]$, where E is the expectation.

The generated models, extracted from the training data, are used to generate random samples during hypothesis testing of the Monte Carlo simulation method. Since annotation is sometimes time intensive, the models for the landmarks p may be generated synthetically from a recipe or theoretical expectations from the centrifugation process.

During the verification/testing phase of the method, samples for the level points may be randomly generated from the distribution model and thus synthetically generate a potential fluid layer structure including hypothesized levels for LA, SB or SG and BG. From the calibration step we can have knowledge about the tip reference point 212B. The liquid-air interface LA is derived from the transition between air and serum or plasma portion 212SP. The top fluid level HT may be derived from a single or a plurality of views since correspondences between the rows is available. Similar to the training phase, the fluid height HT is normalized to one and normalized ratios are therefore drawn to generate a fluid layer structure.

An efficient method is used to generate random samples from a multi-variate Gaussian level model by using a decomposition of the second order statistics e.g. the covariance matrix $\Sigma$ into $\Sigma=AA^T$ using Cholesky decomposition by assuming a positive definite matrix, e.g., using preconditioning. A set of independent standard normal variates z may be generated and applied to generate samples from the modeled fluid level distribution: $x=\mu+Az$. In our case x=(x1, $x2)^T$ denotes a two dimensional vector composed of the normalized scalar values for the fluid level HT. In our case $x=(x1,x2)^T$ denotes a two dimensional vector composed of the normalized scalar values for the fluid level HT.

This structure hypothesis defined by x is verified by aggregating (e.g., integrating) confidence values within the normalized image regions. The verification is performed for the regions (serum or plasma portion 212SP, gel separator 313, if present, and settled blood portion 212SB). Confidences are robustly aggregated using mean/variance computation to overcome missing data, e.g., in the case of occlusions. Between the top fluid level HT and the first hypothesis for the level point at SB or SG we assume to find high responses for serum and plasma portion 212SP. Between the two level landmarks SG and BG we expect a high response for gel separator 313. Between the lower landmark SB or BG and the reference point (tube tip 212B) a reliable layer model expects high confidence values for settled blood portion 212SB.

The best fitting fluid layer model maximizes the corresponding confidence values by minimizing the standard deviation of values. For efficient computation a lookup table may be generated to establish the link between the normalized fluid space and image domain. Additionally, an efficient data structure may be used, i.e. integral images to enable quick hypothesis testing. The verification may include a single image but may also consider multi-view information from multiple cameras 440A-440C for robustness. Since correspondences at the row level are known, the integration is straightforward during aggregation of the confidences.

From the Monte Carlo simulation method, a most likely fluid level structure with respect to serum or plasma portion 2121SP, gel separator 313, and settled blood portions 212SB may be found, i.e., determination of LA, SB or LA, SG and BG. Another refined testing could include a verification of hypothesis by consideration of HDR imagery, i.e., by minimizing the standard deviation of spectral responses in these regions. Another refined testing method may include a verification of hypothesis arrived at by the Monte Carlo simulation method by consideration of HDR imagery, such as by minimizing an error between detected horizontal fluid levels, i.e., edge detection, extract from HDR images, and the random hypothesis projected to the image domain. Basic intensity computation would support finding of the best hypothesis.

Figure 8:
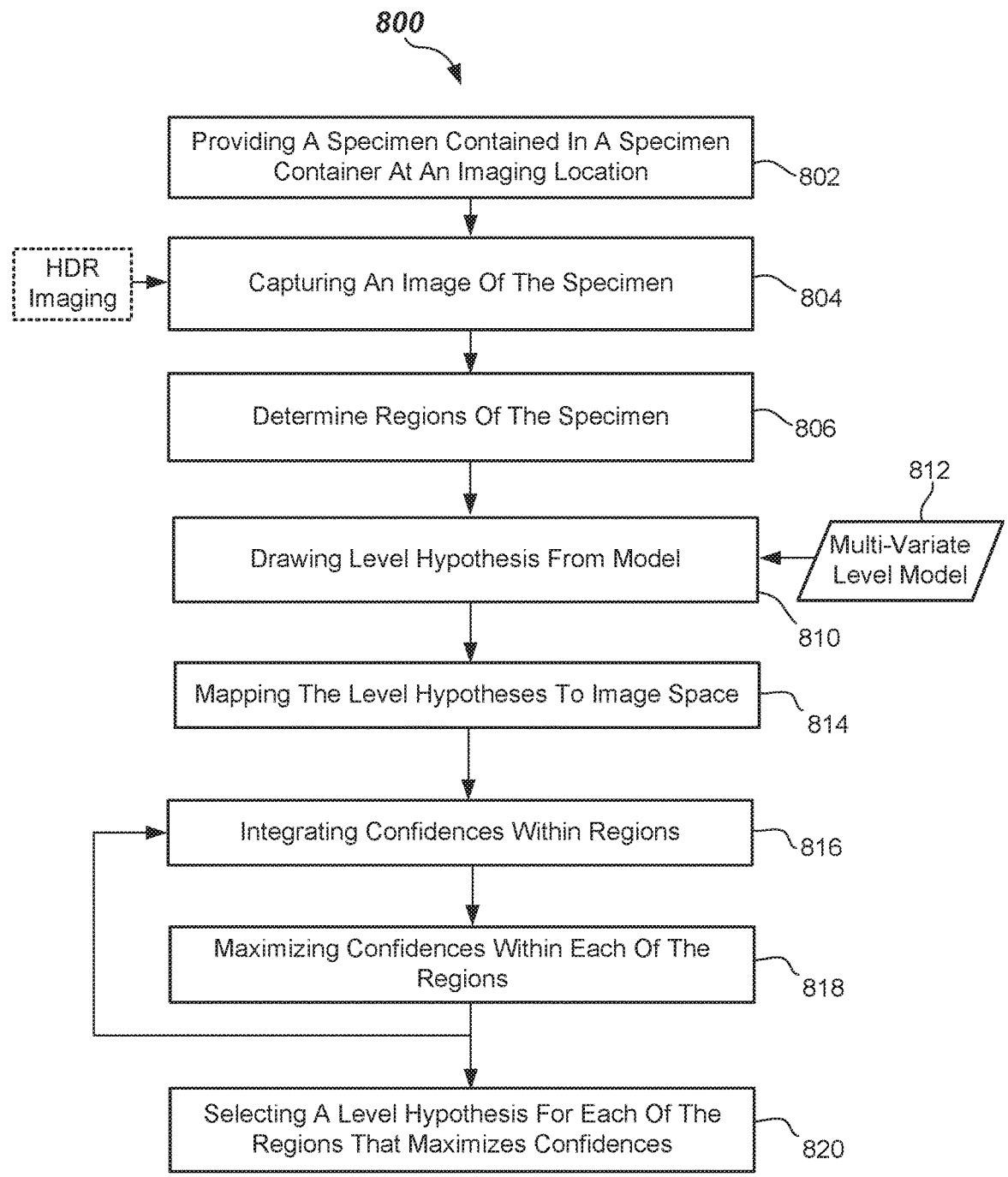
FIG. 8 is flowchart of a Monte Carlo simulation method of quantifying a specimen according to one or more embodiments.

In summary, the Monte Carlo simulation method as described with reference to FIG. 8 can be used to determine segmentation and to quantify a specimen 212 contained within the specimen container 102. The method 800 includes, in 802, providing a specimen 212 contained in a specimen container 102 at an imaging location 441, and in 804, capturing an image of the specimen 212. Image may be captured with a single camera, such as 440A.

The method 800 includes, in 806, determining regions of the specimen 212 including at least a serum or plasma portion 212SP and settled blood portion 212SB. This may be accomplished by the HDR imaging method described herein or by any other suitable segmentation method.

The method includes, in 810, drawing level hypotheses from a multi-variate level model 812. Block 810 involves drawing random level hypothesis generated by the multi-variate level model 812, such as hypothesis for LA and SB if no gel separator 313 is present, and hypothesis for LA, SG, and SB if the gel separator 313 is present.

The method includes, in 814, mapping the level hypotheses to image space. For example, the method may exploit a look up table to project the level hypothesis into the 2D image domain. Next, in 816, the method 800 integrates confidences within the regions. An iterative process takes place between block 818 and block 816 until the confidences are maximized within each of the regions. Finally, the level hypotheses that maximizes the confidences for each region is selected in 820. The Monte Carlo method in one or more embodiments may be used alone for determining segment locations (e.g., LA, and SB or SG) or for verifying the segment locations determined by HDR imaging.

Once the segment locations (e.g., LA, and SB or SG) and VSP are determined in 519, 520, and 528, these quantified values may be used to determine if sufficient fluid is present for the tests ordered, as received from the LIS 147. Further, the segment locations LA and SB or SG from 519-520 may be used to determine where to place the aspiration probe tip so that no settled blood portion 212SB or gel separator 313 are aspirated for any of the aspirations when multiple tests are ordered.

At the quality check module 130 or 130A, once the volume of the liquid region is calculated in 528, a presence of an artifact (e.g., clot, bubble, and/or foam) may be determined by operating on the 2D data subset of the liquid region with one or more artifact classifiers in artifact detection 522. An estimated volume of the artifacts may be subtracted from the available volume VSP, so that a better estimate of the available volume of the liquid is provided when an artifact is present. Artifact detection methods and apparatus are described in co-pending and contemporaneously-filed provisional patent application entitled "METHODS AND APPARATUS FOR CLASSIFYING AN ARTIFACT IN A SPECIMEN." However, in some embodiments, the artifact (e.g., clot, bubble, foam) may be removed from the specimen 212 and then the specimen 212 may be re-quantified according to the quantification method.

Furthermore, once the liquid region is identified in 518, a presence of an interferent (e.g., H, I, and/or L) may be determined by operating on the data subset of the liquid region with one or more interferent classifiers. In one embodiment, a separate classifier may be used for each of H, I, and L as described in co-pending and contemporaneously-filed provisional patent application entitled "METHODS AND APPARATUS FOR DETECTING AN INTERFERENT IN A SPECIMEN." If a high index of hemolysis, icterus or lipemia is present, the specimen 212 may be discarded without further quantification, or may be redrawn and re-screened. In some embodiments, the specimen 212 may be processed to lower the lipemia level and then re-screened.

Accordingly, it should be apparent that the model-based quantification method 500 carried out by the quality check module 130 or 130A may result in a rapid quantification of the serum or plasma portion 212SP and/or the settled blood portion 212SB of the specimen 212. Final 2D results of each of the viewpoints and determinations can be aggregated across the multiple viewpoints and compared and/or averaged to provide a 3D model.

Figure 6:
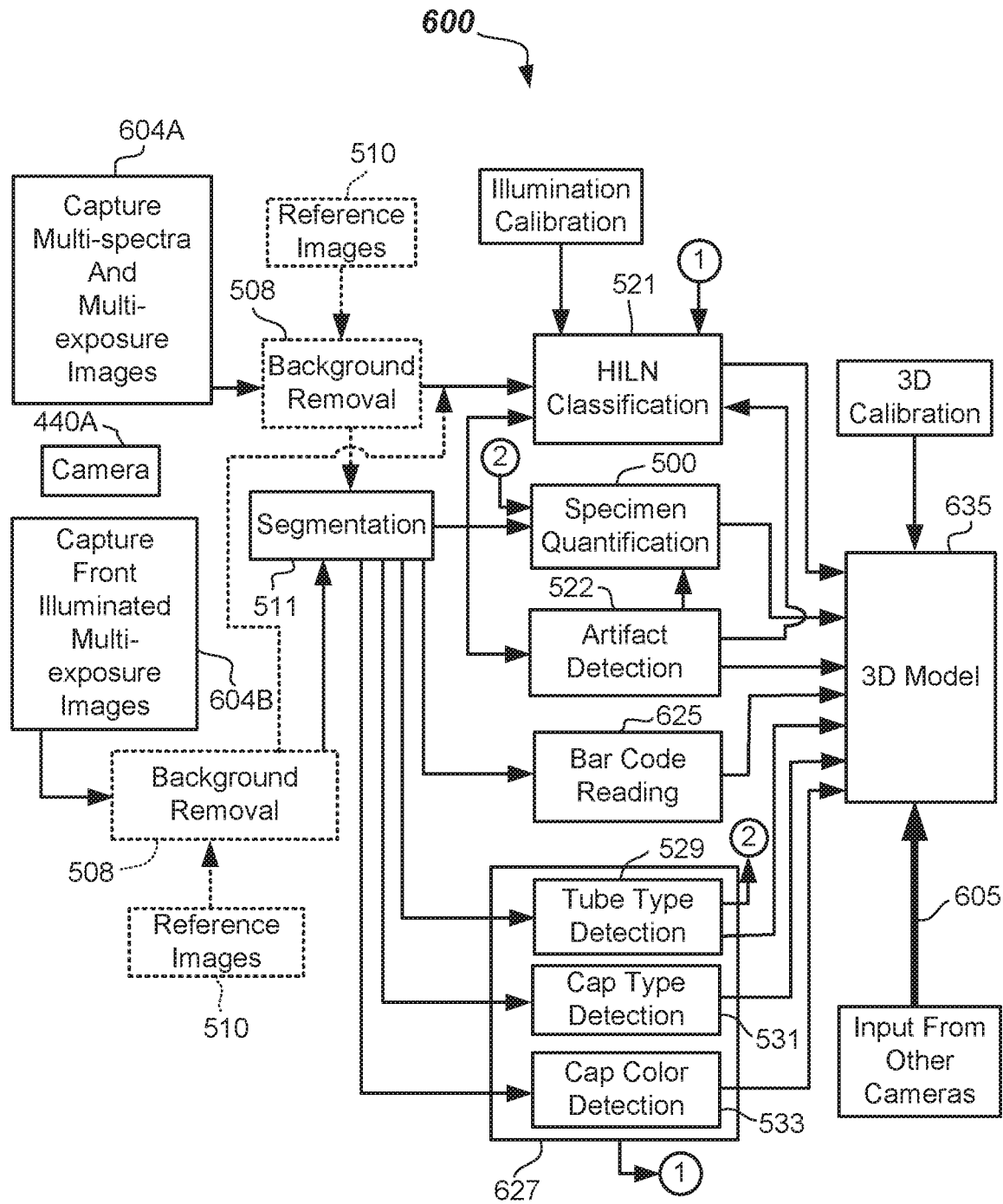
FIG. 6 illustrates a general block diagram of components of a specimen testing apparatus including capability to quantify a specimen as well as the capability to detect characteristics of a specimen or to quantify a specimen container according to one or more embodiments.

FIG. 6 illustrates a flowchart of a broader characterization method 600 wherein the quantification of the specimen 212 is just one of the many items that may be characterized or classified by the broader method 600 using the quality check module 130 or 130A. According to one or more embodiments of the method 600, images are captured, such as by multiple cameras (camera 440A is shown). However, other cameras 440B, 440C may be used to capture images from the other viewpoints, such as is shown in FIGS. 4A and 4C. The processing that will be described for the images captured on camera 440A is identical for the other cameras 440B, 440C at the other viewpoints and their inputs in line 605 may be used to develop a 3D model of the specimen 212 used for final determinations and/or resolving any differences between the various viewpoints.

The images captured by camera 440A and the other cameras 440B, 440C may be multi-spectral (e.g., RGB) and multi-exposure images, as discussed above. In particular, multiple exposures (e.g., 4-8 or more exposures) may be taken for each spectra of light used in 604A at each viewpoint. The respective images at each exposure and for each spectra and for each camera 440A-440C may be obtained simultaneously using monochrome cameras and backlight light sources 444A-444C as described in FIGS. 4A-4B. Optionally, front illuminated multi-exposure images using a white light sources 444D-444F may be obtained in 604B using a color camera for quality check module 130A. Either a back lighted quality check module 130 or a front lighted quality check module 130A may be used or both.

The images may then be processed in 508 to remove background using reference images 510, as described above in optional background removal method. The images may then be further processed to determine segmentation in 511 in the manner described above. In some embodiments, the images from front lighted cameras 440A-440C (see FIGS. 4C-4D) from 604B may be best used for determining segmentation in 511. However, the images captured in 604B could be used for HILN detection in 521, as well. Likewise, any images captured in 604A may be best used for characterization of HILN in 621. However, images captured in 604A could be used for segmentation in 511, as well.

Identifying and quantification of the liquid in 500 in accordance with the methods described herein may also be carried out following segmentation in 511. Quantifying the liquid in 500 may involve, as described herein, the determination of certain physical dimensional characteristics of the specimen 212 such as a physical locations of LA, SB or SG and/or BG, and/or determination of HSP, HSB, and/or HTOT, and/or a volume or depth of the serum or plasma portion (VSP) and/or a volume or depth of the settled blood portion (VSB) as discussed above. The inner width (Wi) may be obtained from the specimen container characterization in 627.

To provide an even closer measurement of the actual volume of serum or plasma portion 212SP that is available for testing, or simply to flag the presence of an artifact, an artifact detection method may be employed in 522 to identify a presence of clot, bubble, or foam. The respective estimated volume of the one or more artifacts present may be subtracted from the estimated volume of the serum or plasma portion VSP determined above in 522 to obtain a better volume estimate. The image data may then be processed using artifact classifiers to determine the presence or absence of an artifact in the serum or plasma portion 212SP in 522. Those pixels identified as an artifact by artifact detection 522 may then be ignored in the quantification method described herein, but also in the HILN classification in 521. Detection of an artifact may also initiate a remediation in some embodiments. Artifact detection method is described in US Application filed contemporaneously and entitled "Methods And Apparatus For Classifying An Artifact In A Specimen."

The results of the segmentation in 511 can also be used to identify the label 218, which may include the identification information 215, such as a barcode. The barcode may be read in 625. Conventional barcode reading software may be used once the label 218 is identified in the segmentation in 511. If a particular image does not contain enough of the barcode to be read, the barcode can be read from, or in conjunction with the other images obtained from other cameras 340B, 340C.

Further characterization of the specimen container 102 may also be accomplished according to the broader method 600 in 627. The characterization of the tube type in 529, cap type in 531, and/or cap color in 533 may be fed to the 3D model 635 to verify that the same characterization was achieved based on processing the images from each camera 440A-440C. If slightly different values are obtained, then the values may be averaged or otherwise aggregated. All of the outputs from the HILN classification in 521, specimen quantification in 500, artifact detection in 522, and specimen container detection in 627 may be fed into the 3D model 635 wherein the 3D model 635 that may be used for final decision making, characterization, and harmonization of the results from the various cameras 440A-440C, and that may be displayed on a monitor or otherwise reported.

Figure 7:
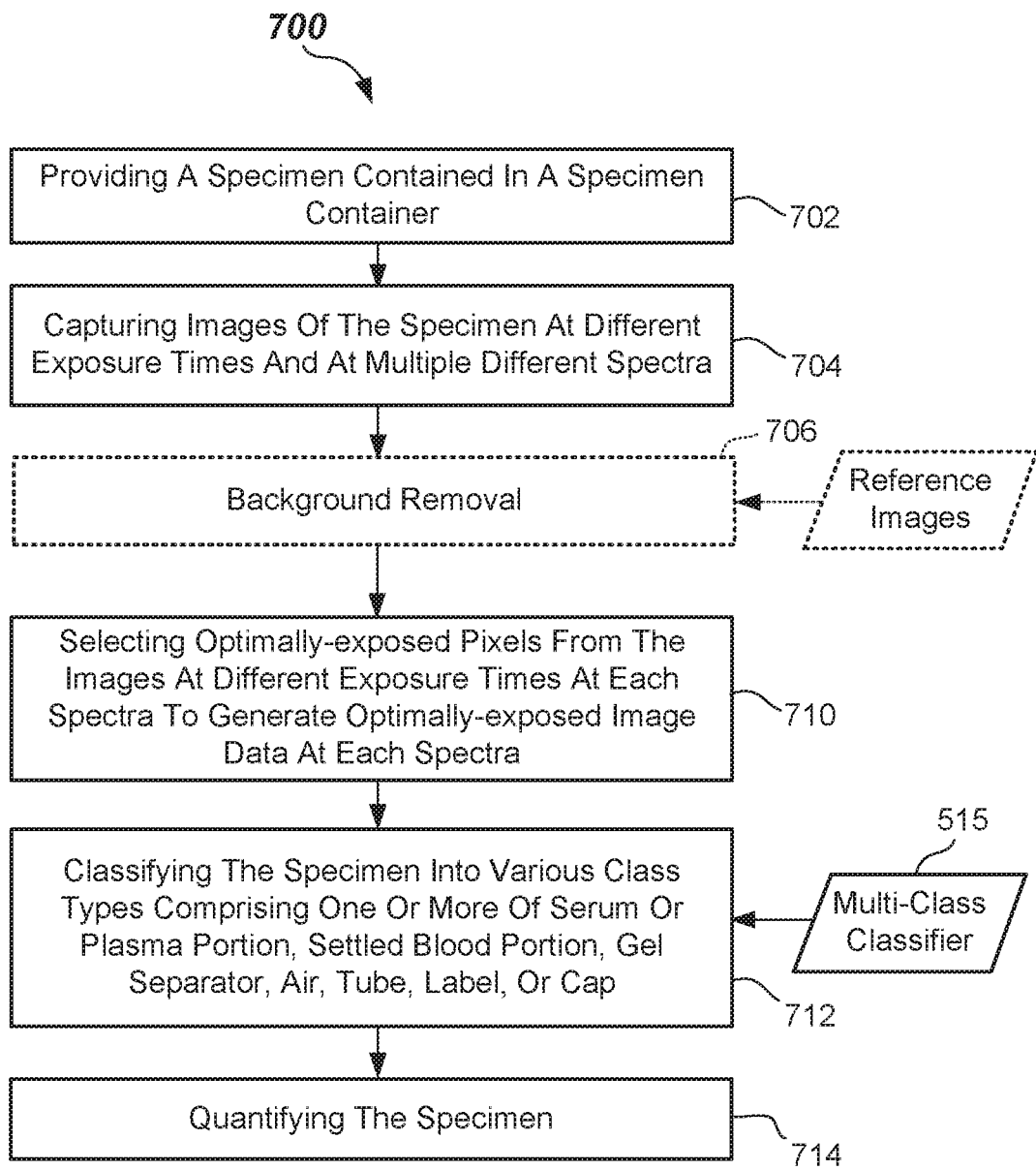
FIG. 7 is flowchart of a method of quantifying a specimen according to one or more embodiments.

FIG. 7 illustrates a flowchart of a method of quantifying a specimen 212 in a specimen container 102 according to one or more embodiments. The method 700 includes providing a specimen (e.g., specimen 212) contained in a specimen container (e.g., specimen container 102, such as a capped, blood collection tube) in 702. Next, the method 700 includes capturing images of the specimen container 102 containing specimen 212 at different exposures (e.g., exposure times) and at multiple spectra having different nominal wavelengths in 704. For example, there may be 4-8 or more different exposures taken at different exposure times in some embodiments, but under the same lighting conditions for each spectra. In one or more embodiments, images may be captured using white light and using front lighting. In other embodiments, images may be captured using a plurality of spectra with narrow-band light sources, such as red, blue and green as backlit light sources 444A-444C. The white light images may be resolved into R, G, and B images as captured by the computer 143, as discussed above. In each instance, the images may be taken by multiple cameras 440A-440C from multiple viewpoints.

The method 700 may optionally include, as shown in 706, background removal to subtract the background in order to lower computational burden. Background removal may be accomplished as part of a calibration process. Reference images may be taken at the same exposure times as for the images of the specimen container 102, but may be captured without a specimen container 102 or the carrier 122.

The method 700 may include, in 710, selecting optimally-exposed pixels from the images at different exposure times at each of the multiple spectra to generate optimally-exposed image data at each spectra. For each corresponding pixel location in each image at a particular spectra, the best exposed pixel (not under or over exposed) is selected and normalized. The optimal exposure range may be as discussed above. This selecting optimally-exposed pixels takes place in an image consolidation phase (e.g., image consolidation 512). Thus, for each of the RGB spectra for each camera, a 2D data set of optimally-exposed pixels may be generated.

Next, the method 700 includes classifying the specimen into various class types comprising one or more of serum or plasma portion 212SP, settled blood portion 212SB, gel separator 313, air 212A, tube 212T, label 218, or cap 214. Classifying may be accomplished by computing statistical data of the optimally-exposed pixels at the different wavelengths to generate statistical data, and then operating on the statistical data of the optimally-exposed pixels with a multi-class classifier 515 to identify the classes present in the data set.

Next, the method 700 includes quantifying of the specimen in 714 by determining one or more of: a location of a liquid-air interface LA between the air 212A and the serum or plasma portion 212SP, a location of a serum-blood interface SB between the serum or plasma portion 212SP and the settled blood portion 212SB, a location of a serum-gel interface SG between the serum or plasma portion 212SP and the gel separator 313, a location of a blood-gel interface BG between the settled blood portion 212SB and the gel separator 313, a volume VSP and/or a depth HSP of the serum or plasma portion 212SP, or a volume VSB and/or a depth HSB of the settled blood portion 212SB.

Accordingly, based on the foregoing it should be apparent that a model-based specimen quantification method 700 carried out by a quality check module 130, 130A may result in a rapid quantification of the specimen 212 L. While the quality check module 130 has been shown in FIG. 1 as being located such that the pre-screening is performed immediately after centrifugation on the centrifuge 125, it may be advantageous to include this feature directly on an analyzer (e.g., analyzer 106, 108, and/or 110) in some embodiments, or elsewhere. Furthermore, in some embodiments, the centrifugation may be performed prior to loading the racks 104 into the loading area 105, so that in some embodiments, the quality check module 130 may be located at the loading area 105 and the quality check can be carried out as soon as the robot 124 loads a specimen container 102 into a carrier 122. Optionally, quality check module 130A may be provided in the same locations as quality check module 130. In some embodiments, one quality check module 130A dedicated to quantification may be used at one location while another quality check module 130 dedicated to HILN detection may be provided at a different location.

While the invention is susceptible to various modifications and alternative forms, specific system and apparatus embodiments and methods thereof have been shown by way of example in the drawings and are described in detail herein. It should be understood, however, that it is not intended to limit the invention to the particular apparatus or methods disclosed but, to the contrary, the intention is to cover all modifications, equivalents, and alternatives falling within the scope of the invention.

What is claimed is:

1. A method of quantifying a specimen contained within a specimen container, comprising:
   providing a specimen;
   capturing images of the specimen at multiple spectra having different nominal wavelengths, and at multiple different exposures;
   selecting optimally-exposed pixels from the images at the multiple different exposures and at each of the multiple spectra to generate optimally-exposed image data for each of the multiple spectra, wherein the selected optimally-exposed pixels have an intensity value within a predetermined upper portion of a pixel intensity range;
   classifying, using the optimally-exposed pixels, the specimen into various class types comprising one or more of serum or plasma portion, settled blood portion, gel separator, if the gel separator is used, air, tube, label, or cap; and
   quantifying the specimen by determining one or more of:
   a location of a liquid-air interface between the air and the serum or plasma portion,
   a location of a serum-blood interface between the serum or plasma portion and the settled blood portion,
   a location of a serum-gel interface between the serum or plasma portion and the gel separator, if the gel separator is used,
   a location of a blood-gel interface between the settled blood portion and the gel separator, if the gel separator is used,
   a volume or a depth of the serum or plasma portion, or a volume or a depth of the settled blood portion.

2. The method of claim 1, wherein the capturing images of the specimen at the multiple spectra and the multiple exposures times is conducted from multiple different viewpoints, with a camera provided at each viewpoint.

3. The method of claim 2, wherein the multiple different viewpoints comprise three or more viewpoints.

4. The method of claim 1, wherein the specimen is a centrifuged specimen including the settled blood portion and the serum or plasma portion.

5. The method of claim 1, wherein the classifying the specimen is based upon a multi-class classifier.

6. The method of claim 5, wherein the multi-class classifier is generated from multiple training sets.

7. The method of claim 5, wherein the multi-class classifier further comprises a support vector machine.

8. The method of claim 5, comprising identifying:
   the serum or plasma portion,
   the settled blood portion,
   a liquid-air interface between the air and the serum or plasma portion, and
   a serum-gel interface or a serum-settled blood interface, depending on if a gel separator is present.

9. The method of claim 1, comprising identifying a location of a liquid-air interface between the air and the serum or plasma portion.

10. The method of claim 1, comprising identifying a location of a serum-settled blood interface.

11. The method of claim 1, comprising identifying a location of a serum-gel interface.

12. The method of claim 1, comprising calculating a volume of the serum or plasma portion.

13. The method of claim 1, comprising calculating a volume of the settled blood portion.

14. The method of claim 1, comprising determining a physical dimensional characteristic of the specimen container.

15. A method of quantifying a specimen contained within a specimen container, comprising:
   providing a specimen;
   capturing images of the specimen at multiple spectra having different nominal wavelengths, and at multiple different exposures;
   selecting optimally-exposed pixels from the images at the multiple different exposures and at each of the multiple spectra to generate optimally-exposed image data for each of the multiple spectra;
   classifying the specimen into various class types comprising one or more of serum or plasma portion, settled blood portion, gel separator, if the gel separator is used, air, tube, label, or cap;
   quantifying the specimen by determining one or more of:
   a location of a liquid-air interface between the air and the serum or plasma portion,
   a location of a serum-blood interface between the serum or plasma portion and the settled blood portion, a location of a serum-gel interface between the serum or plasma portion and the gel separator, if the gel separator is used, a location of a blood-gel interface between the settled blood portion and the gel separator, if the gel separator is used, a volume or a depth of the serum or plasma portion, or a volume or a depth of the settled blood portion; and verifying segmentation of the specimen into various class types by a Monte Carlo simulation method.

16. A quality check module adapted to quantify a specimen, comprising:

a plurality of cameras configured to capture images of the specimen at multiple spectra having different nominal wavelengths, at multiple exposures, and from different viewpoints; and a computer configured and operable to:

select optimally-exposed pixels from the images at the different exposures and at each of the multiple spectra to generate optimally-exposed image data for each of the multiple spectra, wherein the selected optimally-exposed pixels have an intensity value within a predetermined upper portion of a pixel intensity range, classify, using the optimally-exposed pixels, the specimen into various class types comprising one or more of serum or plasma portion, settled blood portion, gel separator, if the gel separator is used, air, tube, label, or cap, and quantify the specimen by determining one or more of:

a location of a liquid-air interface between the air and the serum or plasma portion, a location of a serum-blood interface between the serum or plasma portion and the settled blood portion, a location of a serum-gel interface between the serum or plasma portion and the gel separator, if used, a location of a blood-gel interface between the settled blood portion and the gel separator, if used, a volume or a depth of the serum or plasma portion, or a volume or a depth of the settled blood portion.

17. A specimen testing apparatus, comprising:

a track; and a quality check module on the track, the quality check module including:

a plurality of cameras configured to capture images of the specimen at multiple spectra having different nominal wavelengths, at multiple different exposures, and from different viewpoints, and a computer configured and operable to:

select optimally-exposed pixels from the images at the multiple different exposures at each of the multiple spectra to generate optimally-exposed image data for each of the multiple spectra, wherein the selected optimally-exposed pixels have an intensity value within a predetermined upper portion of a pixel intensity range, classify, using the optimally-exposed pixels, the specimen into various class types comprising one or more of serum or plasma portion, settled blood portion, gel separator, if the gel separator is used, air, tube, label, or cap, and quantify the specimen by determining one or more of:

a location of a liquid-air interface between the air and the serum or plasma portion, a location of a serum-blood interface between the serum or plasma portion and the settled blood portion, a location of a serum-gel interface between the serum or plasma portion and the gel separator, if the gel separator is used, a location of a blood-gel interface between the settled blood portion and the gel separator, if the gel separator is used, a volume or a depth of the serum or plasma portion, or a volume or a depth of the settled blood portion.

* * * * *